(12) United States Patent
Cope

(10) Patent No.: US 7,968,282 B2
(45) Date of Patent: Jun. 28, 2011

(54) METHODS FOR REMOVAL OF SPECIFIC SEED TISSUE OR STRUCTURE FOR SEED ANALYSIS

(75) Inventor: Jason Cope, Ankeny, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 12/545,417

(22) Filed: Aug. 21, 2009

(65) Prior Publication Data
US 2010/0050300 A1 Feb. 25, 2010

Related U.S. Application Data

(60) Provisional application No. 61/090,950, filed on Aug. 22, 2008, provisional application No. 61/092,863, filed on Aug. 29, 2008.

(51) Int. Cl.
*C12Q 1/00* (2006.01)
(52) U.S. Cl. .............................. 435/4; 356/318; 47/58.1
(58) Field of Classification Search ...... 435/4; 356/318; 47/58.1 SE
See application file for complete search history.

(56) References Cited

U.S. PATENT DOCUMENTS

| | | | |
|---|---|---|---|
| 2,675,942 A | 4/1954 | Vogelsang | |
| 3,363,486 A | 1/1968 | Tourison | |
| 3,884,347 A | 5/1975 | Gallagher et al. | |
| 5,835,206 A * | 11/1998 | Tragesser | 356/72 |
| 6,327,090 B1 | 12/2001 | Rando et al. | |
| 6,368,806 B1 | 4/2002 | Openshaw et al. | |
| 6,472,185 B2 | 10/2002 | McCasky Feazel et al. | |
| 6,562,698 B2 | 5/2003 | Manor | |
| 7,024,817 B2 | 4/2006 | Zehner et al. | |
| 7,227,065 B2 | 6/2007 | Hoffbeck et al. | |
| 7,502,113 B2 | 3/2009 | Deppermann et al. | |
| 7,591,101 B2 | 9/2009 | Deppermann | |
| 7,611,842 B2 | 11/2009 | Deppermann et al. | |
| 7,703,230 B2 | 4/2010 | Curry et al. | |
| 2005/0210744 A1 | 9/2005 | Watanabe et al. | |
| 2006/0046244 A1 | 3/2006 | Depperman | |
| 2006/0048248 A1 | 3/2006 | Depperman | |

(Continued)

FOREIGN PATENT DOCUMENTS

DE  19616216 A1  10/1997

(Continued)

OTHER PUBLICATIONS

Santong et al., "Serial Extraction of Endosperm Drillings (SEED)—A Method for Detecting Transgenes and Proteins in Single Viable Maize Kernels", Plant Molecular Biology Reporter 19:151-158 (2001).

(Continued)

*Primary Examiner* — Susan B McCormick Ewoldt
(74) *Attorney, Agent, or Firm* — Alston & Bird LLP

(57) ABSTRACT

A method for reducing resources for selecting seed to be produced in commercial quantities or for research is disclosed. Samples of seed which are candidates for selection are collected and given an identifier. Specific tissue or structure from candidate seed is removed. A test or analysis is performed on the candidate seed or the removed tissue or structure. Results of the test or analysis are recorded and correlated to the seed's identifier. The results are evaluated and a decision is made whether to select a candidate seed for commercial production or for research. Time, space, and labor associated with growing plants in an experimental plot or greenhouse and taking tissue samples from growing plants is saved.

17 Claims, 16 Drawing Sheets

U.S. PATENT DOCUMENTS

| | | |
|---|---|---|
| 2007/0204366 A1 | 8/2007 | Depperman et al. |
| 2007/0207485 A1 | 9/2007 | Depperman et al. |
| 2008/0131254 A1* | 6/2008 | Cope et al. .................. 414/754 |
| 2008/0131924 A1 | 6/2008 | Cope et al. |
| 2009/0077932 A1 | 3/2009 | Cope et al. |
| 2009/0155878 A1 | 6/2009 | Becker et al. |
| 2009/0215060 A1 | 8/2009 | Deppermann et al. |
| 2010/0044381 A1 | 2/2010 | Goldman |

FOREIGN PATENT DOCUMENTS

| | | |
|---|---|---|
| EP | 0611604 A3 | 8/1994 |
| EP | 1126268 A1 | 8/2001 |
| GB | 2293744 A | 4/1996 |
| WO | 8001531 A1 | 8/1980 |
| WO | 03100381 A1 | 12/2003 |
| WO | WO 03/100381 A1 | 12/2003 |
| WO | 2007103769 A2 | 9/2007 |
| WO | WO 2008/064019 A2 | 5/2008 |

OTHER PUBLICATIONS

Krone, "Genetic Analysis and Breeding for Kernel Methionine Content in Maize (*Zea mays* L.)", Thesis submitted to Univ. of Minn. Gratuate School Faculty (Aug. 1994). 127 pages.

Holscher, D. et al., *Application of Laser-Assisted Microdissection for Tissue and Cell-Specific Analysis of RNA, Proteins, and Metabolites*, Progress in Botany, vol. 69, Dec. 2007, pp. 141-167.

International Search Report for Application No. PCT/US2009/054546 mailed Apr. 6, 2010.

International Search Report for International Application No. PCT/US2009/054541, mailed Apr. 5, 2010.

* cited by examiner

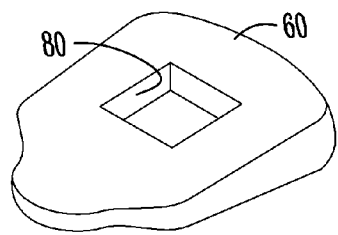 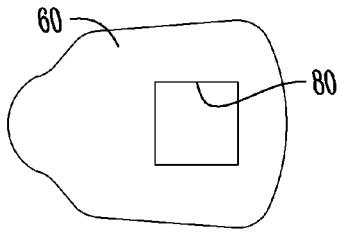 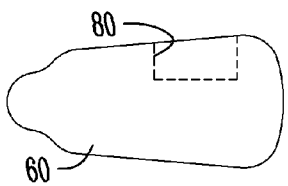
*Fig.9A*  *Fig.9B*  *Fig.9C*
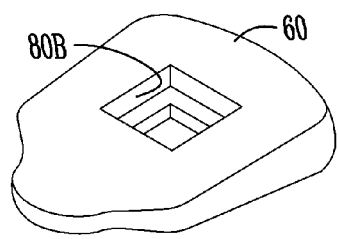 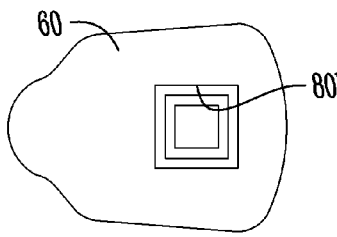 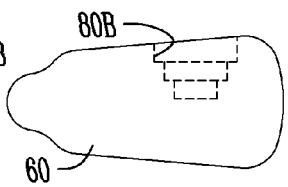
*Fig.10A*  *Fig.10B*  *Fig.10C*
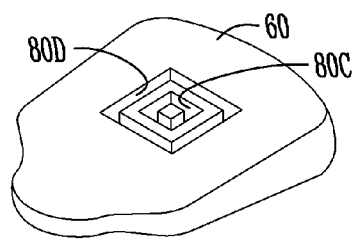 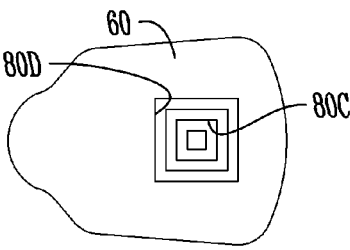 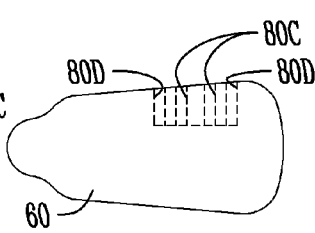
*Fig.11A*  *Fig.11B*  *Fig.11C*

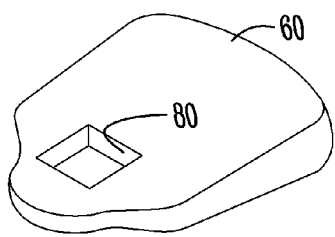
*Fig.12A*
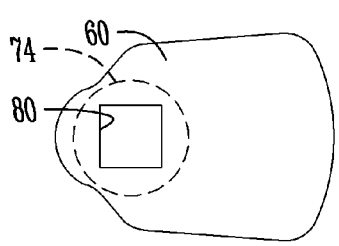
*Fig.12B*
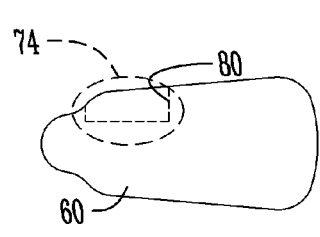
*Fig.12C*
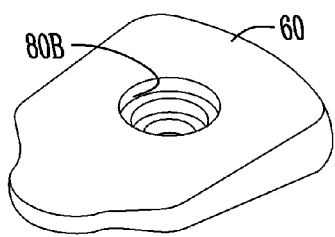
*Fig.13A*
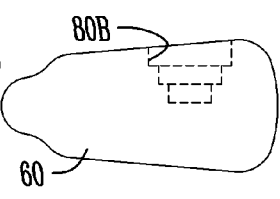
*Fig.13B*
*Fig.13C*
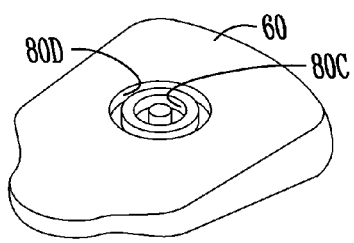
*Fig.14A*
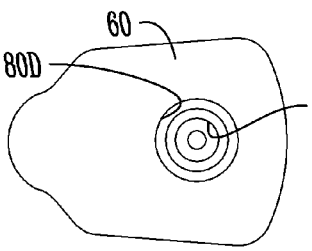
*Fig.14B*
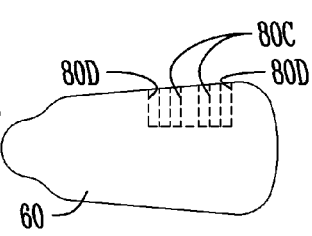
*Fig.14C*

US 7,968,282 B2

METHODS FOR REMOVAL OF SPECIFIC SEED TISSUE OR STRUCTURE FOR SEED ANALYSIS

RELATED APPLICATIONS

This application claims priority under 35 U.S.C. §119 to provisional application Ser. Nos. 61/090,950 filed Aug. 22, 2008 and 61/092,863 filed Aug. 29, 2008, which applications are hereby incorporated by reference in their entirety.

I. BACKGROUND

A. Field of the Invention

The present invention relates to methods for analyzing seed and to make decisions about the seed and its subsequent use based on the analysis, and in particular, methods for efficient and effective removal of specific seed tissue or structure to enable testing and analysis of the seed or its removed tissue or structure.

B. Problems in the Art

A primary goal of seed companies is to develop seed that grow into plants that are commercially desirable to crop producers. Seed companies devote substantial resources towards research and development of commercially desirable seed.

Conventional research and development techniques tend to be laborious and require vast amounts of land and space. All or much of the seed involved in the research is planted in research plots. After plants emerge from the seed, tissue samples from each plant are acquired. The tissue samples are transported to a laboratory to deduce information needed for the research and development of the seed and plants from the seed.

These methods are well-known in the industry. The resource costs of land, labor, and machinery are substantial.

Thousands, if not hundreds of thousands, of acres of experimental plots can be utilized. Appropriate numbers of workers and machinery to till, plant, maintain, obtain plant tissue samples, transport to the lab, and conduct analyses at the lab, are substantial. Time is also a factor and cost. Decisions about whether a plant and its seed should be used for producing commercial quantities or seed, or should be used in further research, have to wait until tissue samples from emerged plants are possible.

A typical process is as follows. Seed of known parentage, phenotype, or genotype are planted in experimental plots outdoors or in greenhouses. A statistically valid number of plants must be grown in the fields or greenhouses. This involves substantial physical space and labor. After the plants have emerged, tissue samples are taken from the plant. Tests are conducted to identify the genetic makeup or other characteristics of the sample. This process, of course, takes substantial time. The plants must grow to a point where a tissue sample can nondestructively be taken. The samples must be carefully handled and taken to a laboratory. Genetic testing must be conducted before identification of a gene of interest can be made.

It could be beneficial to have a process whereby access to and testing (genetically or otherwise) of relevant genetic material, or tissues, parts, or structures, could be gained without having to grow plants from the seed. As can be appreciated by the skilled artisan, savings in labor, time and space could be substantial.

Obtaining a tissue sample with relevant cellular material from most growing plants is not difficult. Conventionally, a relatively small portion or sample of tissue from a growing plant is removed with a tool (e.g., manually operated leaf punch). If properly done, the removal of the samples is non-destructive, in the sense that a small leaf punch normally does not materially affect the health or viability of the plant. A leaf punch, for example, is used to remove relevant cells for analysis of the plant. Although such leaf samples are not destructive of the plant and are relatively easy to transport to the laboratory and to store, obtaining a plant tissue sample from the normal quantity of plants in seed company experimental plots remains a huge commitment of labor and time. It requires going to each plant in the growing locations and acquiring the leaf sample.

The seed from which the test plot plants are grown also has relevant cellular material. It is quite another matter, however, to gain access to it and perform tests or assays on it without materially affecting the seed's viability or germination potential. The relatively small size of most seed, and its parts, is one reason. Another is that relevant tissue or structure in some seed is only a subset of the whole seed, and many times is inside an outer cover. This makes it difficult to gain access to or acquire only relevant material. Furthermore, some seed have a make-up which makes non-destructive sampling difficult. The tough exterior layer or tissue, the pericarp, of corn seed is an example. It is difficult to remove without using methods that destroy or damage the seed. Still further, all of these issues are antagonistic to high throughput access to and sampling of multiple seed. Precise removal of specific tissue or structure from a small object to gain access to other specific tissue or structure, and doing so efficiently, presents significant challenges.

Therefore, a need exists in the industry to materially reduce the resources used for evaluating plants and their seed for potential commercial production or further use in plant and seed research and development. There is also a need in the art for methods to remove from and/or gain access to specific tissues or structures of a seed, including in a non-destructive and relatively high throughput way.

II. BRIEF SUMMARY

One aspect of the invention is a method for reducing resources for selecting seed to be produced in commercial quantities. Seed which are candidates for possible selection are collected and each is given an identifier. Specific tissue or structure from a single candidate seed is removed to expose or gain access to specific tissue, part(s), or structure of that candidate seed, or to separate and collect specific tissue, part(s), or structure. A test or analysis is performed on the exposed tissue or the removed tissue of the candidate seed. Results of the test or analysis are evaluated and a decision can be made whether to select that candidate seed type for, e.g., commercial production. The results can be recorded and associated with the seed's identifier. The method avoids the time, space, and labor of growing plants in an experimental plot or greenhouse and taking tissue samples from growing plants. Decisions can be made quickly with relatively high throughput directly from a seed.

An method according to an aspect of the invention can include a seed holder and a tool which cooperate to allow the removal of specific seed tissue or structure. The seed holder isolates a seed from other seed and presents it to the tool for tissue removal. Either the exposed tissue in the seed, or removed tissue from the seed can then be tested.

In another aspect of the invention, a method comprises a controlled laser to ablate, cut, separate, or remove tissue, part(s), or structure from seed to obtain or expose desirable parts of the seed in a relatively rapid and accurate manner, while not materially affecting seed viability or germination potential. Relevant exposed part(s) or tissue of the seed can be tested or analyzed, and/or removed part(s) or tissue of the seed can be tested or analyzed.

In another aspect, a method comprises automated steps or automated components in which plural candidate seed can be moved to a tissue removal station, have specific tissue, part(s), or structure removed, and have either (or both) the remaining seed or its removed tissue tested and evaluated. The test(s) or evaluation (s) can include, but are not limited to, genetic, physical, or chemical analysis on a cellular, molecular, or nanoscale level.

III. BRIEF DESCRIPTION OF THE DRAWINGS

A. Figures

Figure 3:
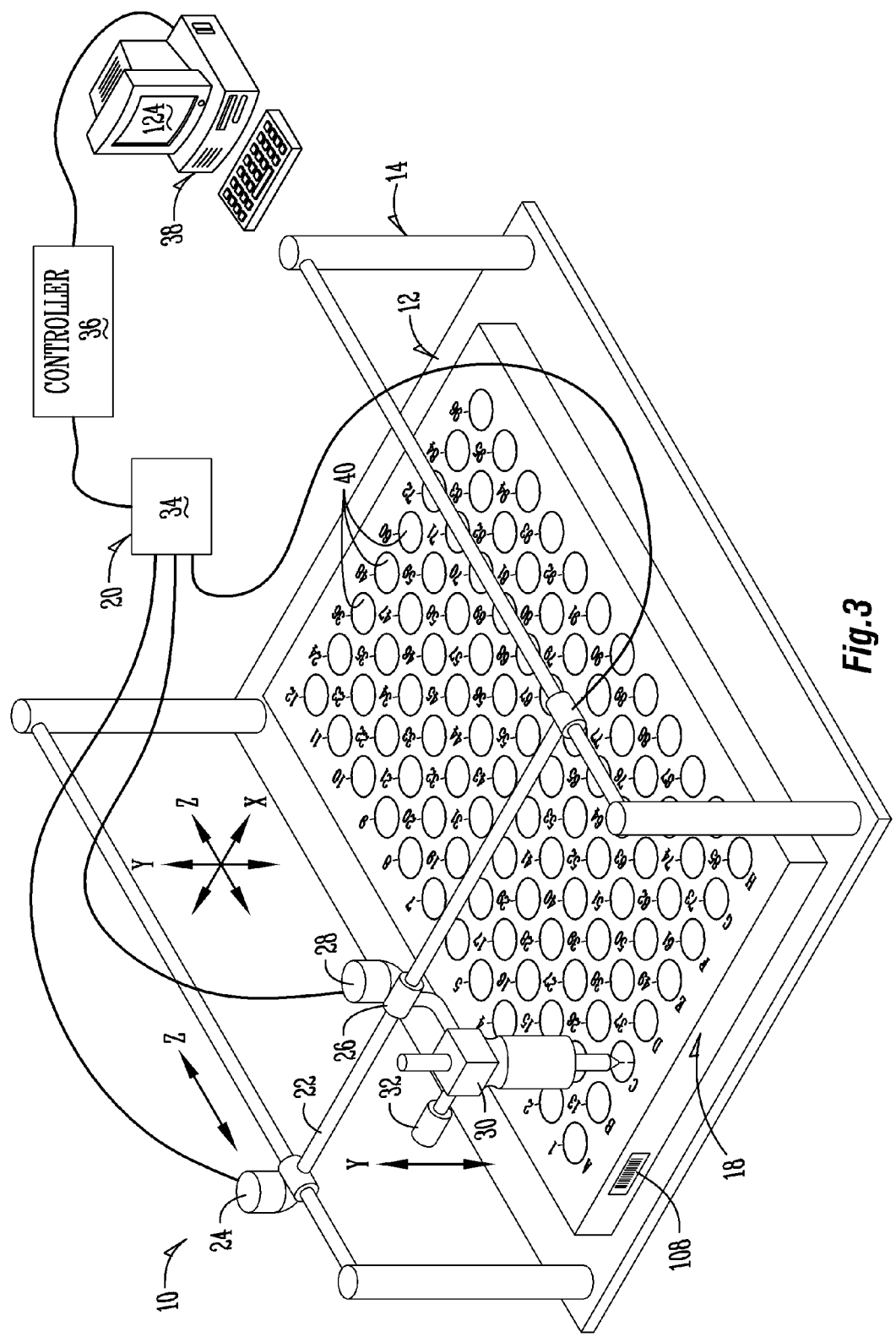
FIG. 3 is a diagrammatic partial perspective view of one aspect of the invention according to Example 1.
Figure 4A:
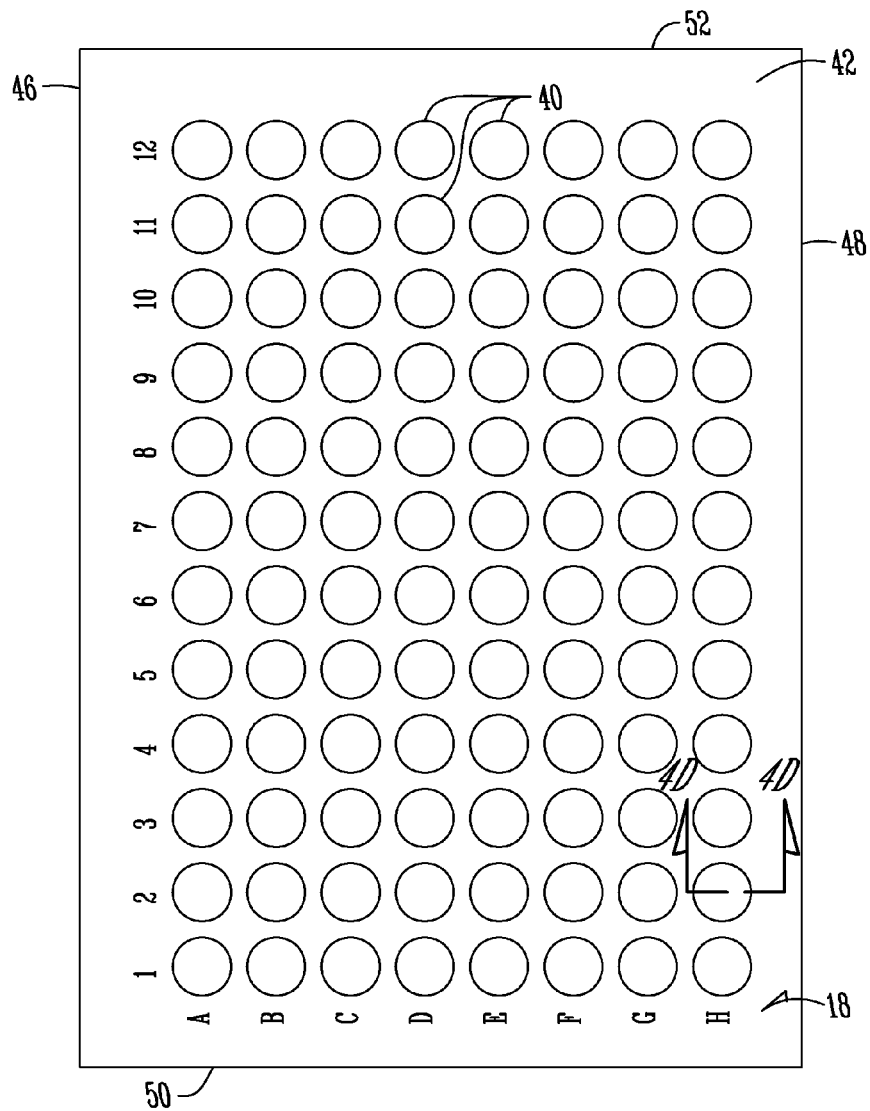
Figure 4B:
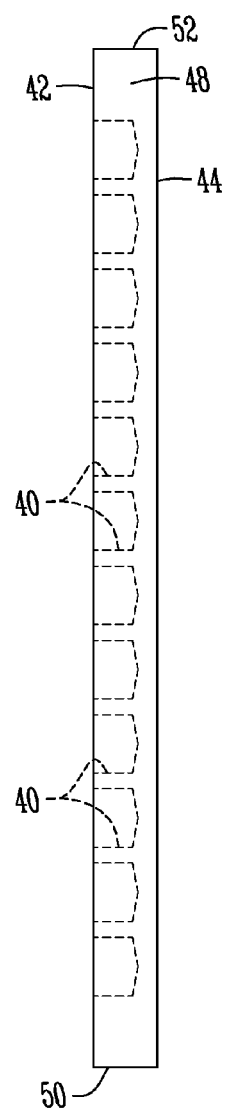
Figure 4C:
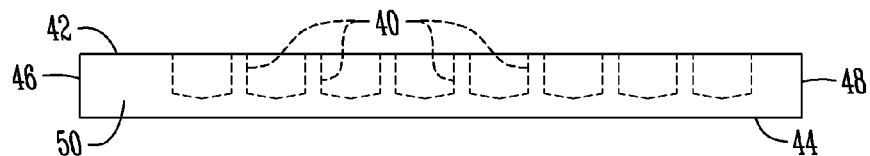

FIGS. 4A-C are plan views of plate 18 of FIG. 3.

Figure 4D:
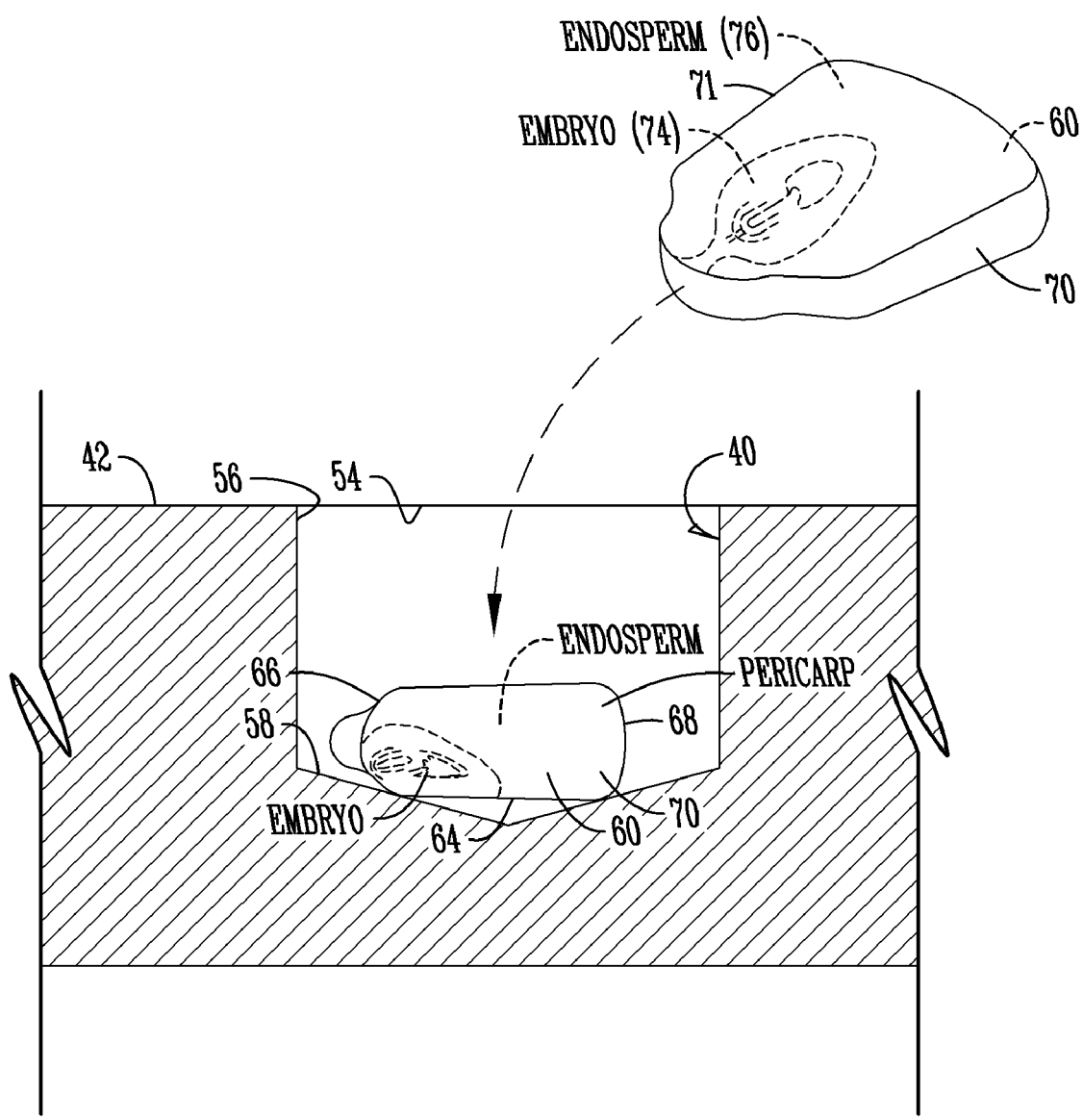

FIG. 4D is an enlarged partial sectional view of one of the wells from plate 18, further showing the positioning of a corn seed in the well.

Figure 5A:
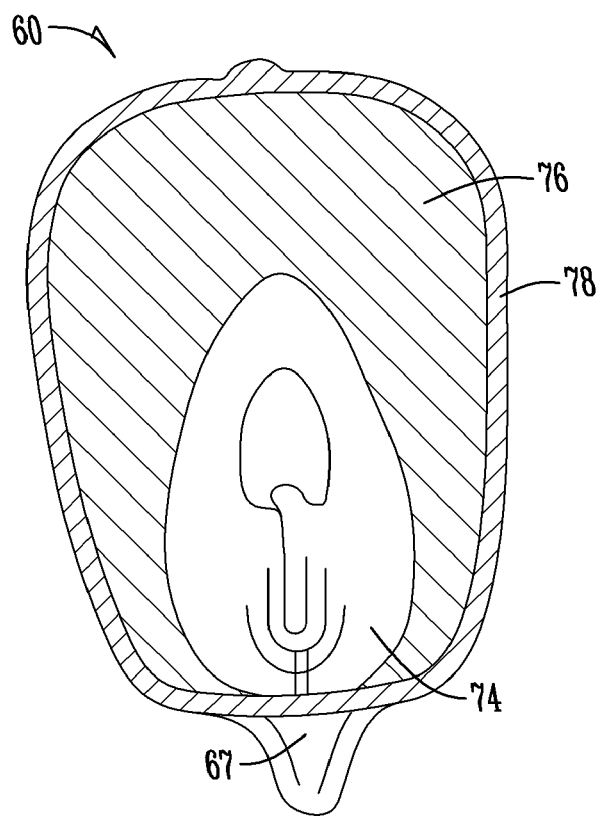
Figure 5B:
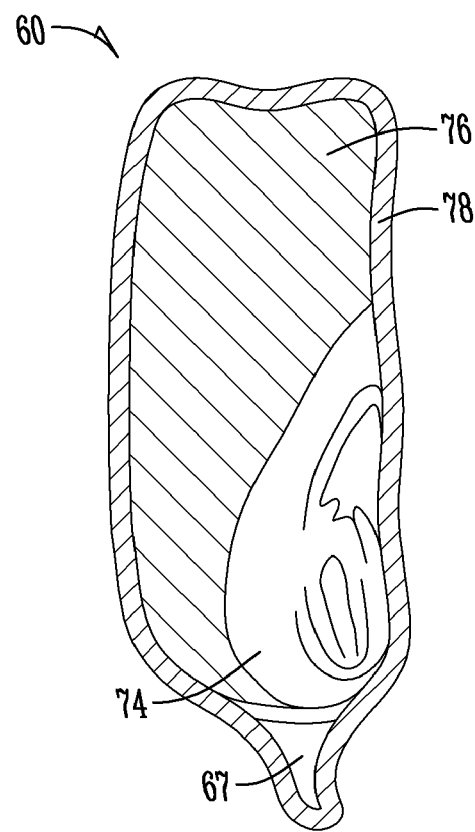

FIGS. 5A and B are enlarged plan and side sectional views of a typical corn seed.

Figure 6A:
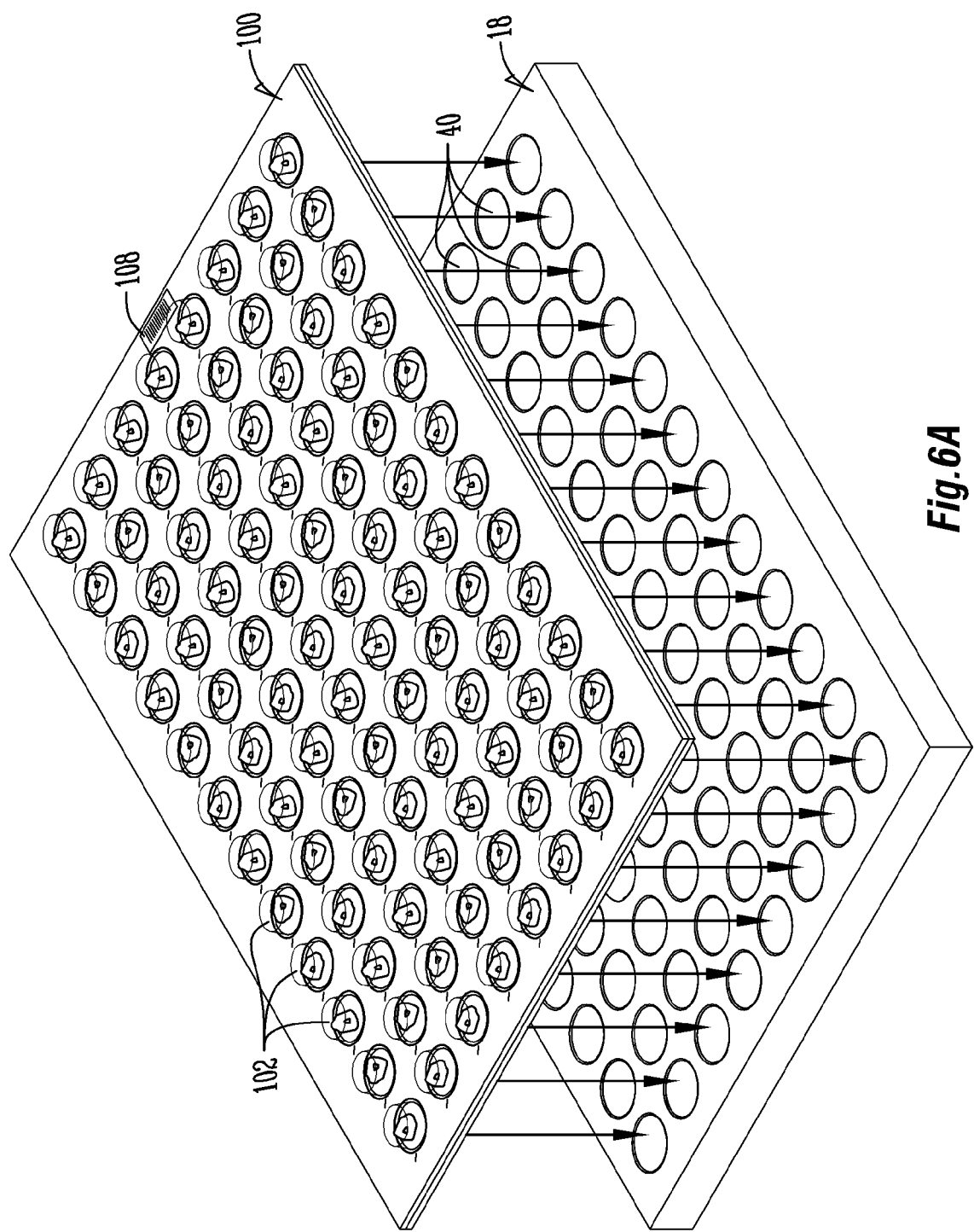

FIG. 6A illustrates one way to deposit a plurality of corn seed in corresponding individual wells of a plate 18 prior to laser ablation.

Figure 6B:
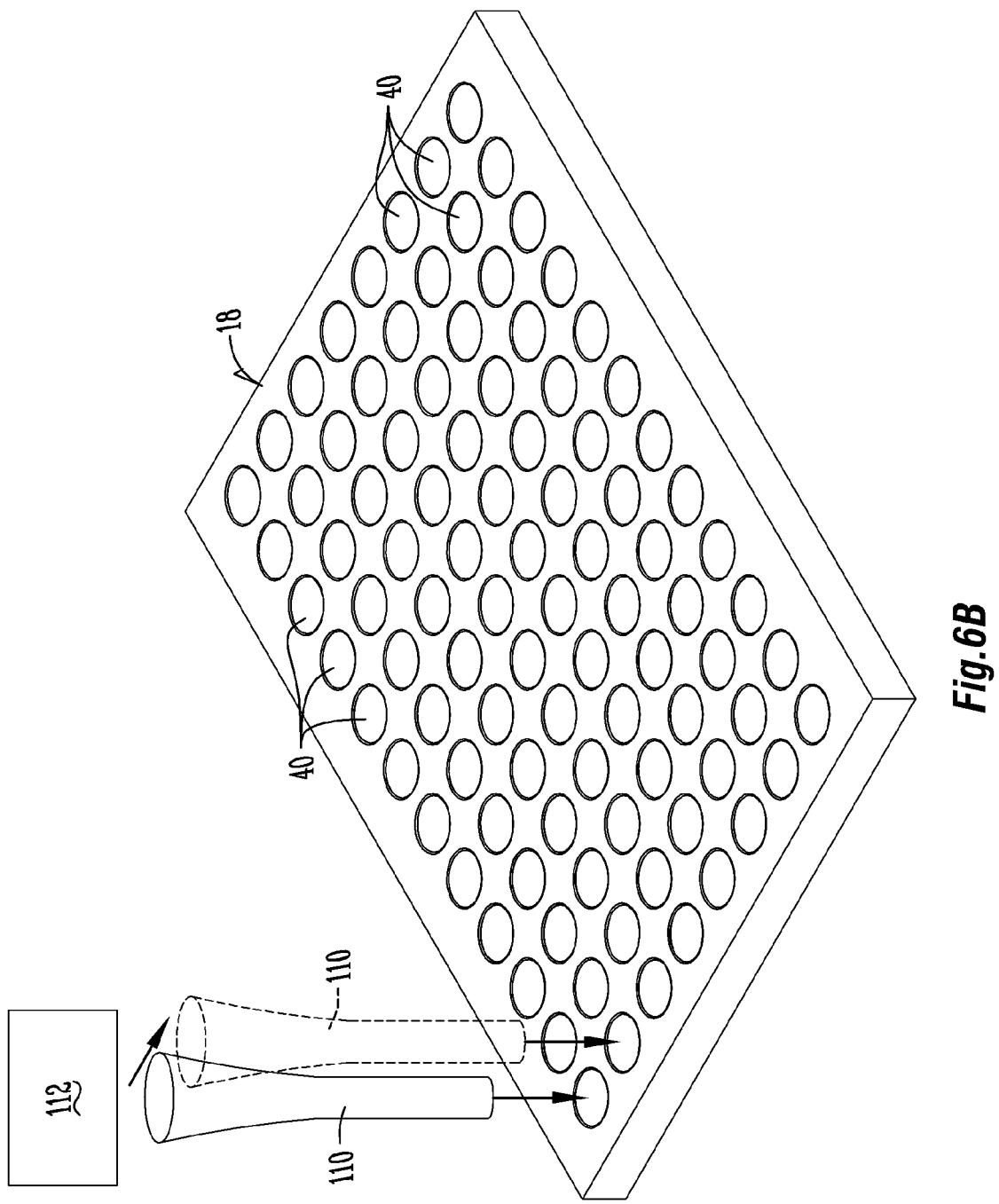

FIG. 6B diagrammatically illustrates an alternative way of depositing a single seed in each of the wells of plate 18.

Figure 7:
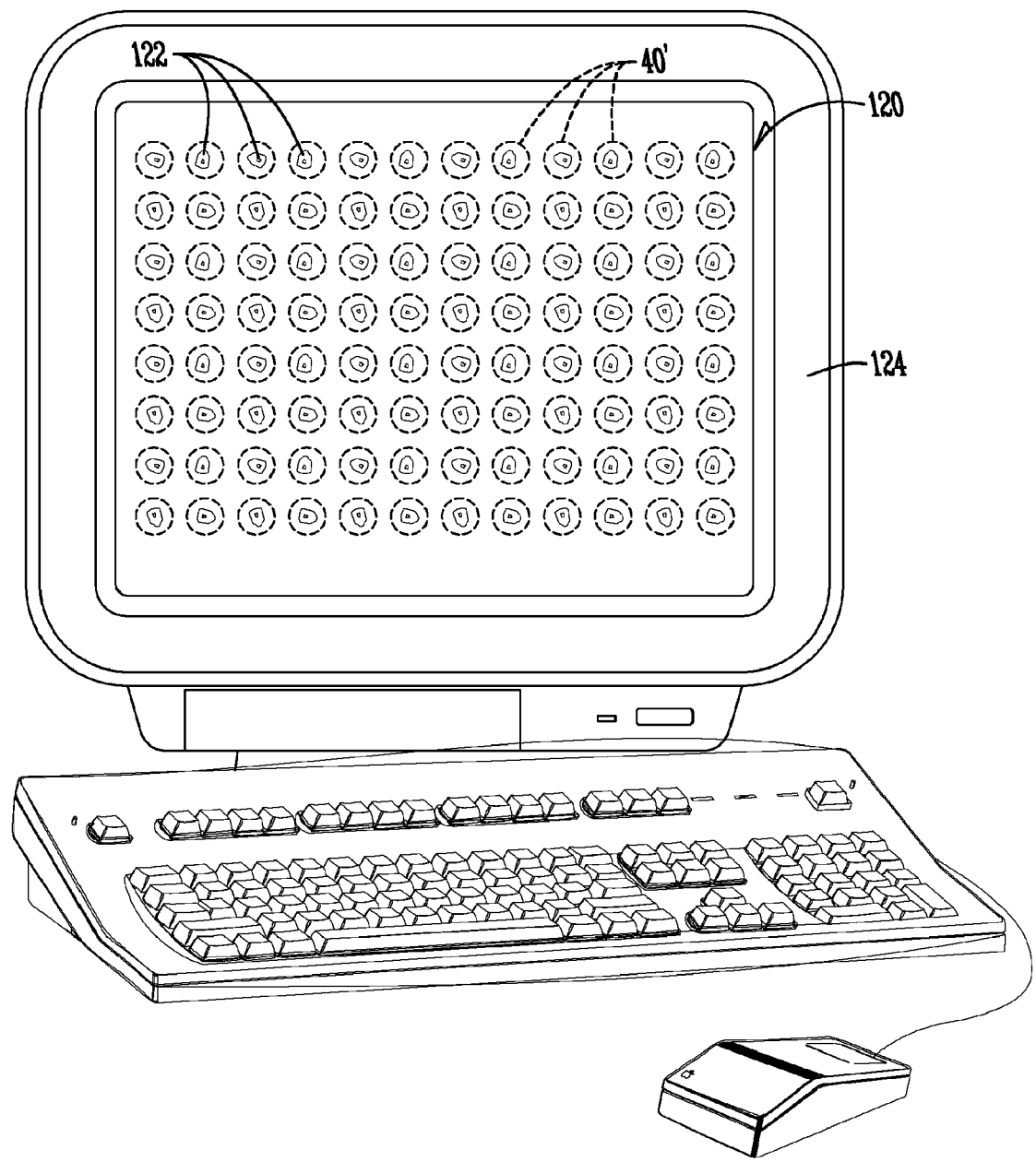

FIG. 7 is a plan view diagram of a software template which allows design of an ablation area for each well of plate 18.

Figure 8A:
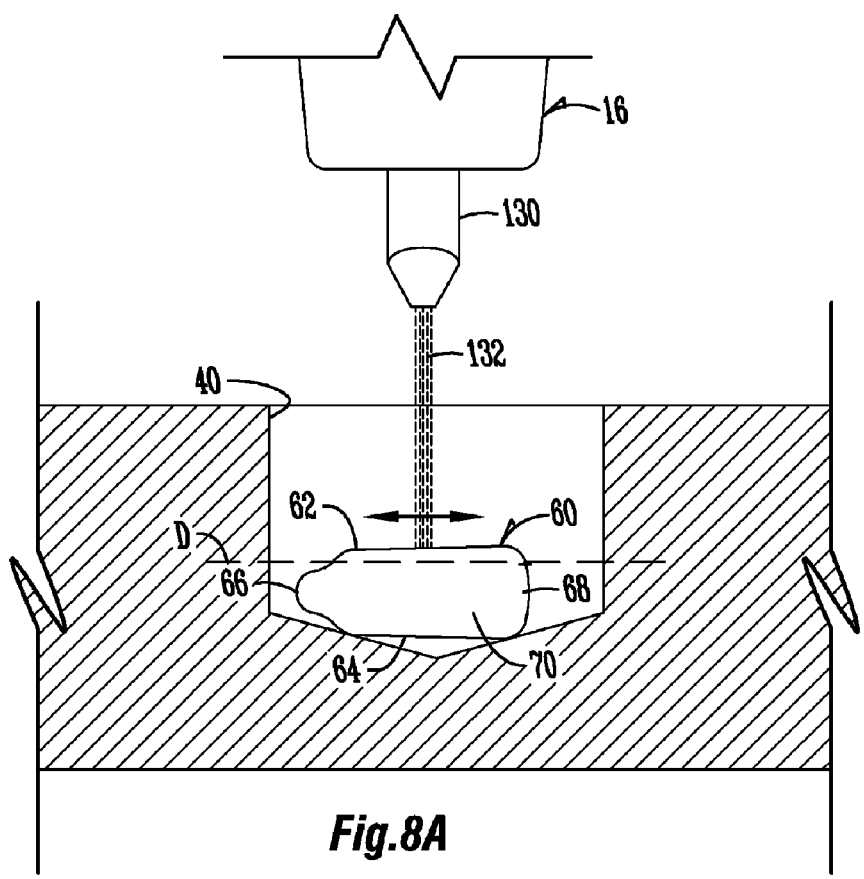

FIG. 8A is an enlarged diagrammatic side elevation view illustrating laser ablation which removes tissue from the seed, leaving a cavity of rectangular prism shape on one surface of the seed.

Figure 8B:
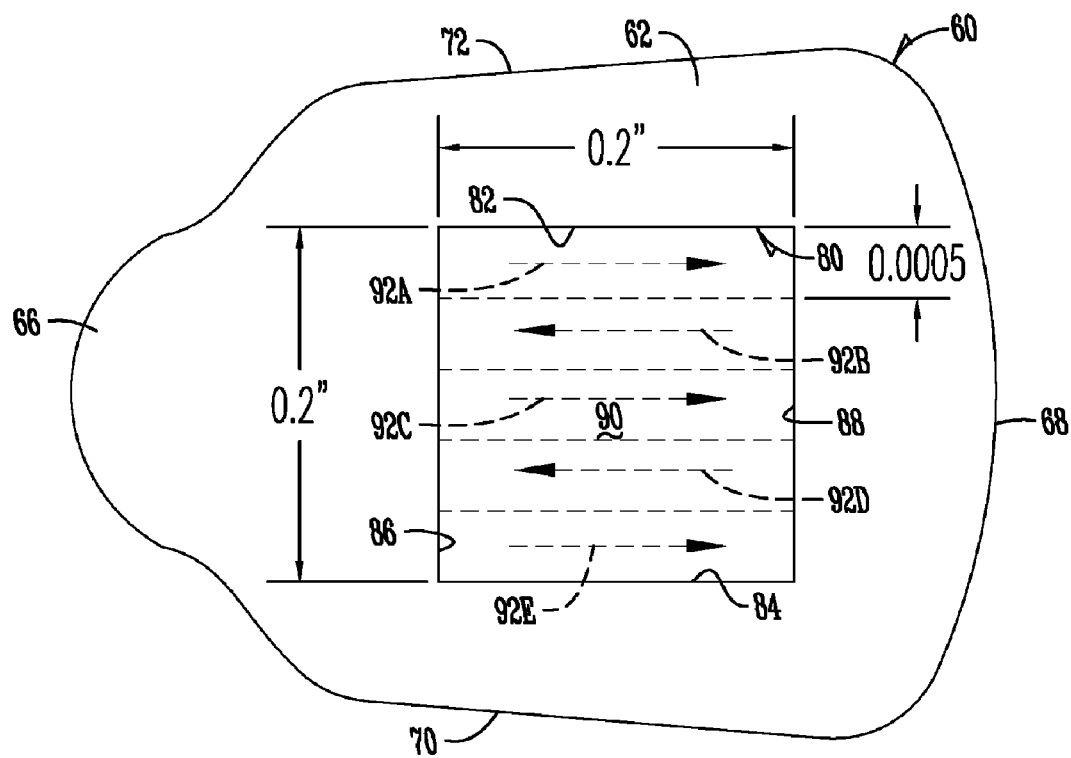

FIG. 8B is an enlarged top plan view of the laser ablated seed of FIG. 8A.

FIGS. 9A-C illustrate various views of a rectangular prism cavity 80 from laser ablation of a seed, in particular, removal of a portion of the pericarp to expose or remove some of the seed endosperm.

FIGS. 10A-C show an alternative ablation pattern for a seed, namely a cavity having a combination of rectangular prism cavities.

FIGS. 11A-C show a still further alternative example of a pattern that can be laser ablated into a single kernel, here a first channel in a rectangular shape and a second channel in a rectangular shape spaced from and around the first channel.

FIGS. 12A-C show various views of another example of a laser-ablated pattern in a seed, here a rectangular prism through the pericarp to expose or ablate a portion of the seed embryo.

FIGS. 13A-C are similar to FIGS. 10A-C but illustrate control of a laser to create a more circular pattern.

FIGS. 14A-C are similar to FIGS. 11A-C but illustrate control of a laser to create circular patterns.

Figure 15:
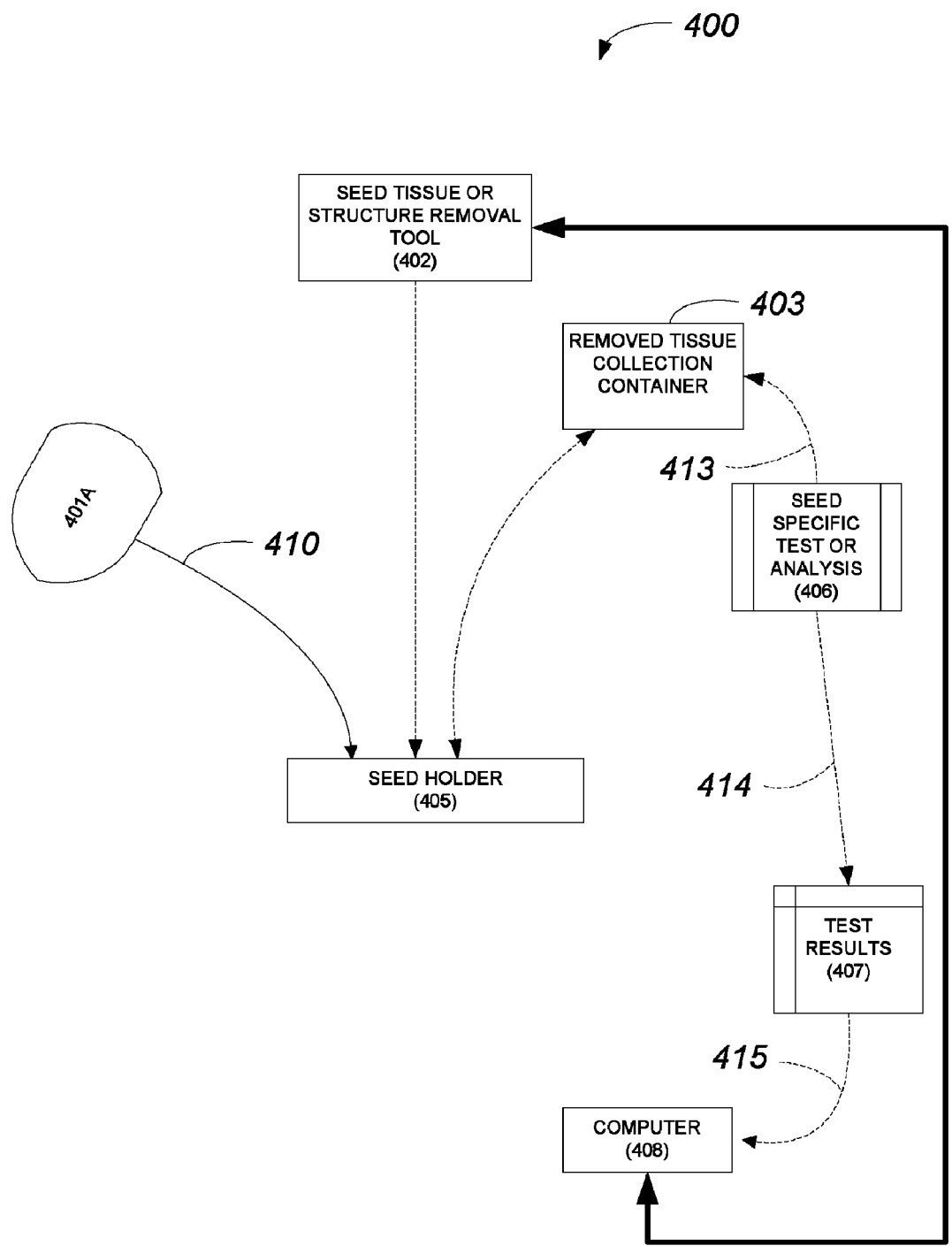

FIG. 15 is a diagrammatic illustration of an Example 2 according to an alternative embodiment of the present invention, where debris from laser ablation of a seed is collected by vacuum into a container where the debris or removed tissue is tested or analyzed as opposed to exposed tissue in the seed.

Figure 16:
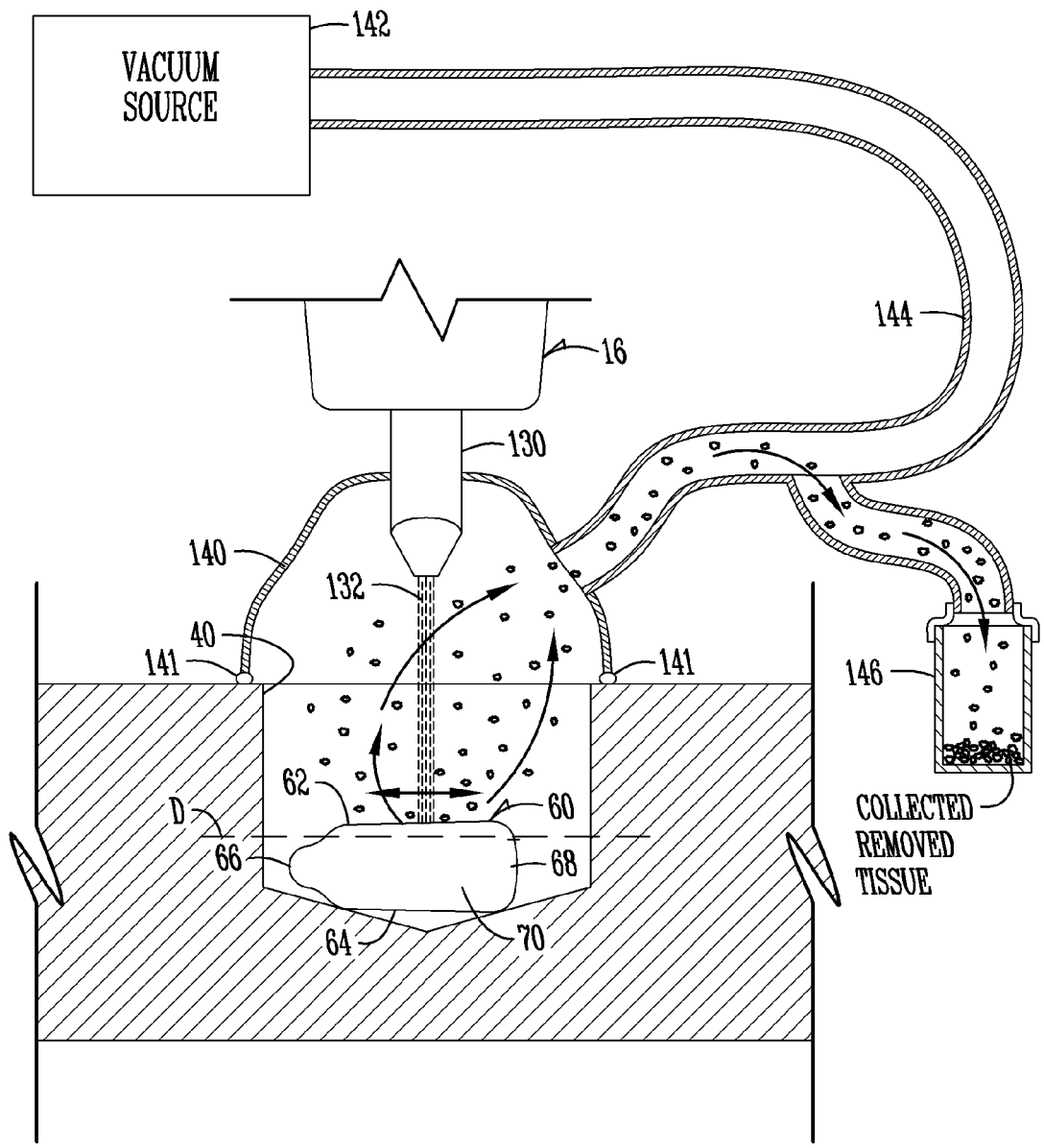

FIG. 16 is a partial sectional, side elevation view of a methodology according to Example 2.

Figure 17:
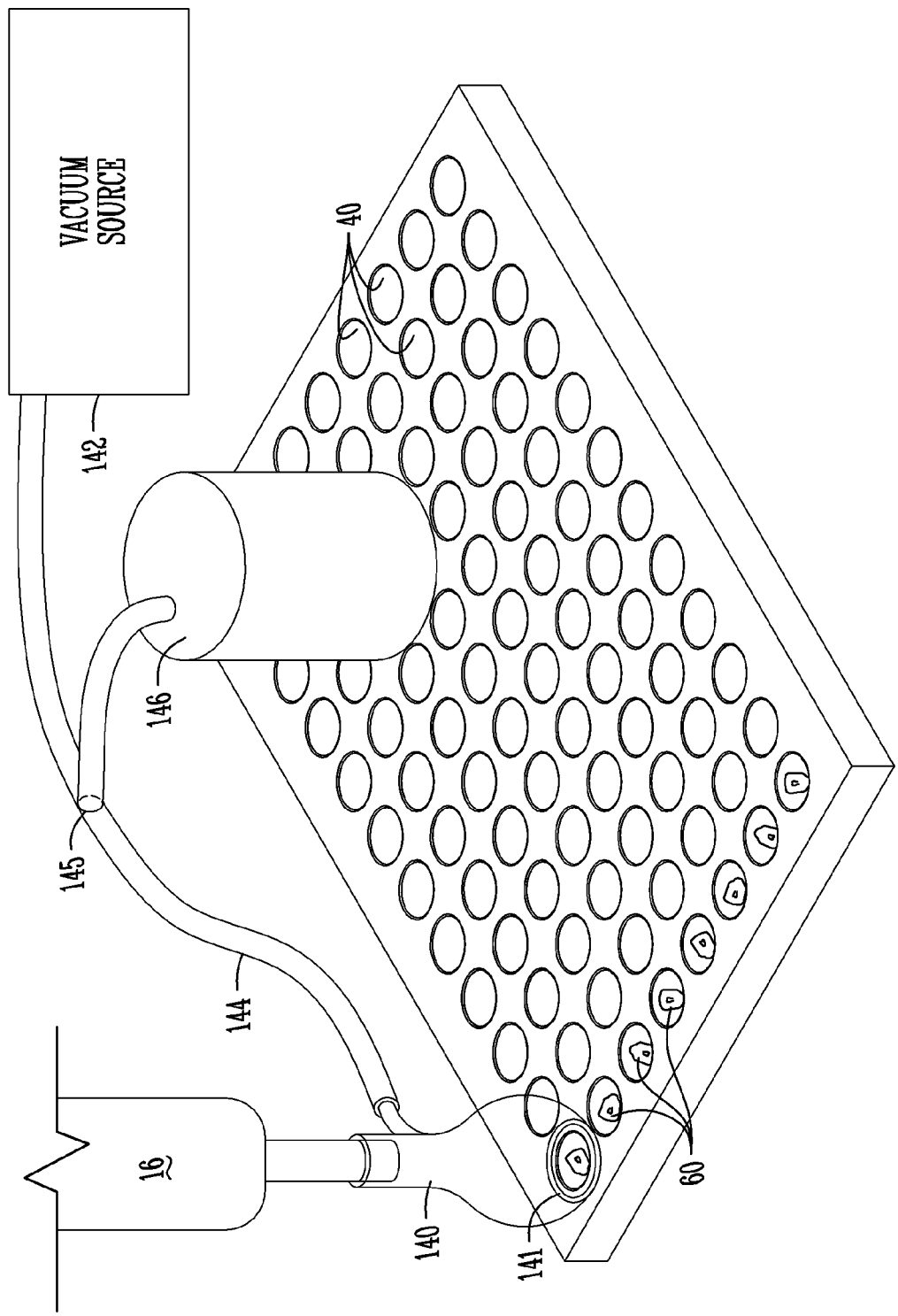

FIG. 17 is a reduced in scale diagrammatic illustration of an optional vacuum system to remove debris generated by laser ablation of a set of seed each positioned in a well of a tray or plate.

Figure 18:
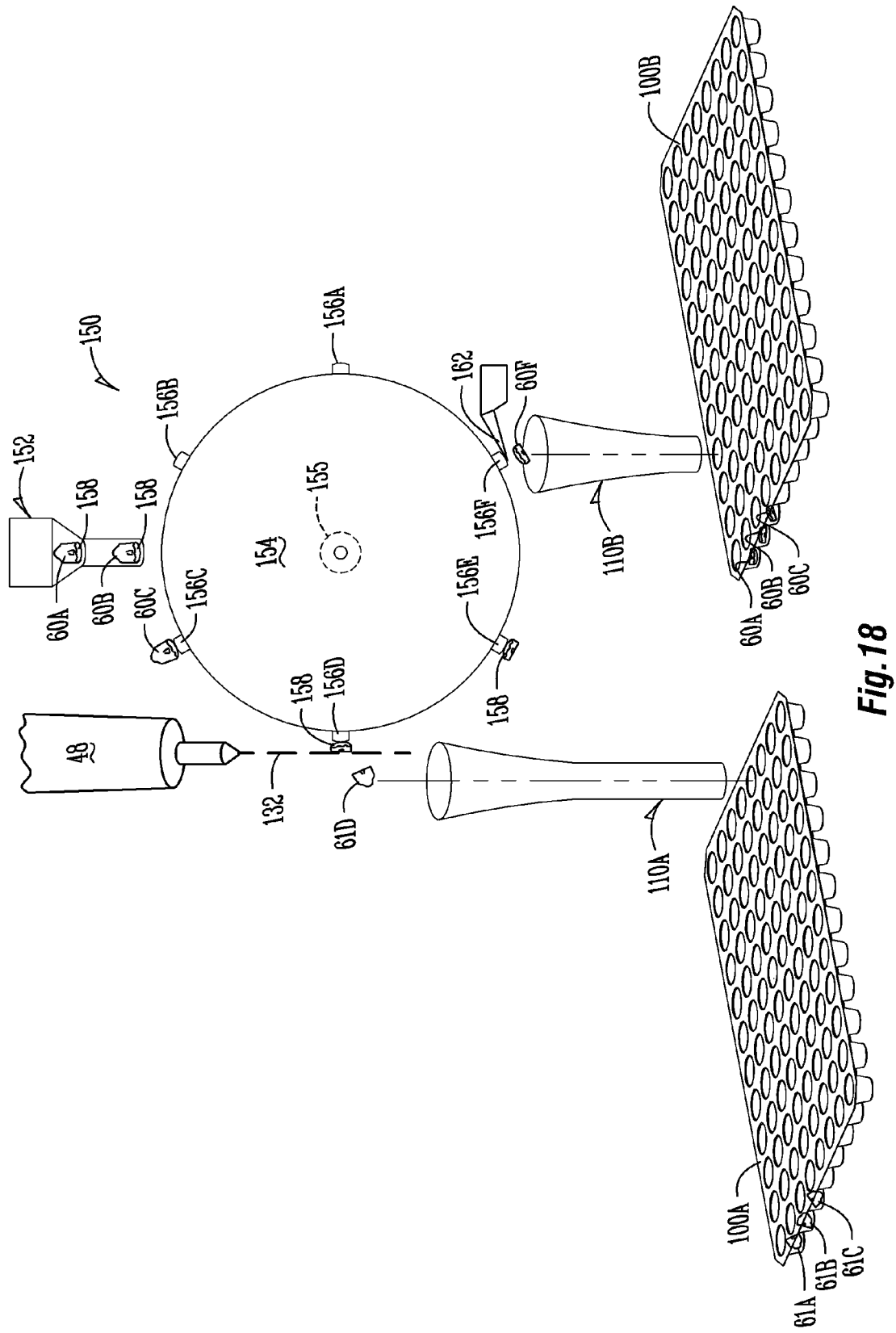

FIG. 18 is a diagrammatic illustration of an optional seed cutter using a laser for cutting, and a seed holding and orientation system based on magnetism.

IV. DETAILED DESCRIPTION

A. Overview

For a better understanding of the invention, several exemplary embodiments of the present invention will be described in detail. Frequent reference will be taken to the accompanying drawings. Reference numerals and letters will be used to indicate certain parts and locations in the drawings. The same reference numerals or letters will be used to indicate the same or similar parts and locations throughout the drawings unless otherwise indicated.

B. Context of the Exemplary Embodiments

The exemplary embodiments described will be primarily in the context of corn and corn seed. It is to be understood, however, that this is but one example of a seed that could be utilized with aspects of the present invention. Additionally, the context of the primary exemplary embodiments is removal of a relatively small amount of tissue or structure of a corn kernel to (a) expose and test specific internal tissue(s) or structure(s) of the seed or (b) test the removed tissue or structure. The removal is intentionally controlled to minimize or avoid detrimental effects to seed viability or germination potential. However, the invention could be used to remove substantially more tissue, even to the point of threatening or destroying seed viability, if an application requires the same.

The embodiments can be applied in analogous ways to other seed. Examples include but are not limited to oat, soybean, wheat, rye, rice, canola, *Brassica* sp., sorghum, sunflower, barley, millet, alfalfa, cotton, peanut, flax, safflower, palm, olive, castor bean, coconut, millet, *arabidopsis*, tobacco, or sorghum seed.

C. Exemplary General Method

Figure 1:
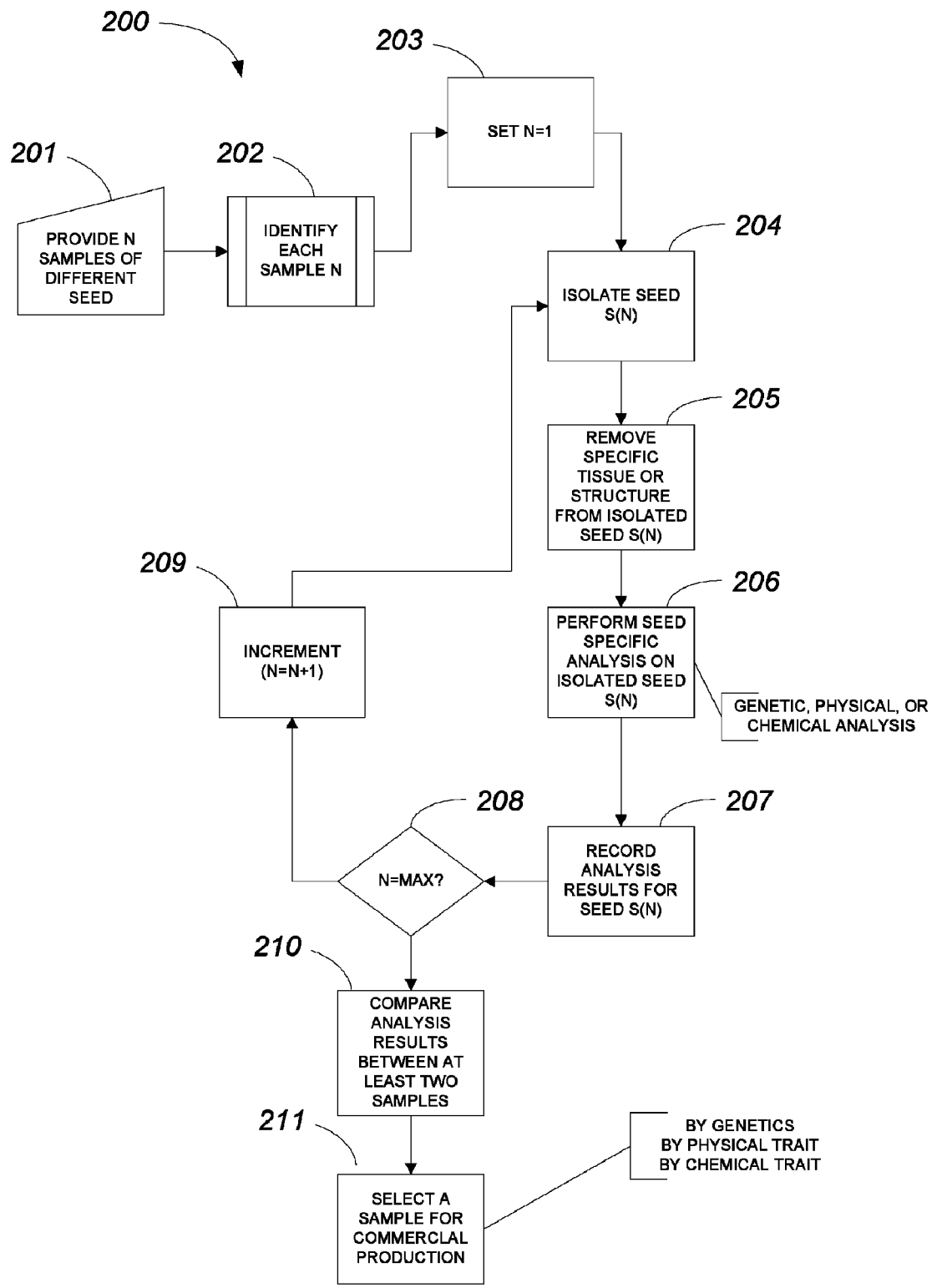
FIG. 1 is a flow chart of a general methodology according to one aspect of the present invention.

FIG. 1 illustrates a general exemplary method 200 according to one aspect of the present invention. Method 200 allows selection of seed to use for further research or commercial production without growing plants from the seed and testing living tissue of the plants. The method can avoid use of land, labor, time, equipment, and materials for growing plants from the seed to then acquire non-destructive samples to analyze for selection decisions. The method can be non-destructive of the seed, allow relatively high throughput of multiple samples, and be substantially automated. Method 200 comprises the following steps.

A plurality of corn kernels of different genotype and/or different corn varieties are analyzed and compared for the purpose of identifying and selecting whether any will be utilized for further research and development or planted to produce commercial or research scale quantities. The method applies as well to other seed specific tests or analysis, such as will be apparent to the skilled artisan.

1. Identification of Candidate Seed (Steps 201/202)

One or more factors are used to decide which seed will be a candidate seed for evaluation (FIG. 1, step 201). In this example, a set of a plurality of individual candidate seed, each having a different trait or genotype and/or corn variety, are pre-selected. Each candidate seed is isolated from the other candidates but with association to information from which the candidate seed can be identified (step 202). That identity can be maintained with each seed through the method. Identification of each seed can be by specific information and/or by some code related to information about or identity of the seed. It can be recorded or stored (e.g., in a computer in a database). Other methods are possible.

Pre-selection of candidate seed can be based on any of a number of factors or criteria. Research scientists select the factors or criteria. Examples of types of factors and criteria are commonly known in the art. Some are genotype, phenotype, parentage, traits, or characteristics. Further discussion of these factors or criteria can be found in such references as: (a) Chahal, G. S & Gosal, S. S., 2002. "Principles and Procedures of Plant Breeding", Alpha Science International, United Kingdom; (b) Falconer, D. S. 1989. "Introduction to Quantitative Genetics". 3rd Ed. Longman. Burnt Mill; and (c) Frisch, M. & Melchinger, A. E., 2005. "Selection Theory for Marker-assisted Backcrossing." Genetics: Published Articles Ahead of Print, published on Mar. 31, 2005 as 10.1534/genetics.104.035451; which are incorporated by reference herein.

2. Isolation of Single Seed (Step 204)

A single candidate seed is isolated by any of a number of ways to present it for removal of specific tissue (FIG. 1, step 204) to gain access to or expose certain specific tissues(s), part(s), or structure(s) of that seed for testing, or collect the removed tissue for testing. For purposes of this description, tissue(s), part(s), or structure(s) of a seed will collectively sometimes be referred to as tissue. One example of isolation is to place the candidate seed into a cavity or well. Another is to grasp, hold, or restrain the seed by or to some device (e.g., with a vacuum; by clamping action). Another is to apply a substance to the seed which is attracted to or held to a surface or member (e.g., adhesive; magnetism). Others are possible. The basic function is to hold the seed for accurate and efficient tissue removal and isolate the seed from others, while maintaining identity of the seed.

3. Removal of Specific Tissue (Step 205)

Tissue of the seed is removed from a specified location of the seed. A number of methods can be used. It can be useful, in certain of the methods, to first orient the seed in a certain manner. This can assist in removal of the specified tissue.

An example of tissue removal is with use of a laser (see FIG. 3). As described in more detail later, a laser can be precisely controlled in intensity. It also can be focused to a beam width that can be effectively used for removing only a relatively small area of tissue from one side of a seed, and to a relatively small, controlled depth.

The laser beam can be operated in a variety of ways to effect tissue removal. An example is programmable raster scanning. The beam is controlled to move at a programmed speed and direction relative to the area to be removed.

The laser beam can be focused upon and moved with precision across the seed to ablate the portion of the seed it strikes and remove tissue. Ablation is defined by one source to remove or destroy especially by cutting, abrading, or evaporating (vaporizing) (Merriam-Webster OnLine Dictionary 2007). Another source describes it as removal of material from the surface of an object by vaporization, chipping, or other erosive processes (WIKIPEDIA. "Ablation" article [on-line], [retrieved on 2008-08-18]. As used herein, ablation refers to such actions, or to analogous actions that remove or separate such seed tissue from the seed. In some instances, this results essentially in a candidate seed having some tissue removed to expose or allow access to internal tissue. The ablation may result in one piece or just a few pieces of removed tissue (more in the sense of cutting or chipping). Alternatively, the ablation may result in the removed tissue being essentially debris (more in the sense of fragments or very small particles, even dust-like, from abrasion, erosive processes, or the like). Alternatively, the ablation may result in the removed material evaporating, sublimating, or forming a plasma.

A laser can function in these manners to remove specific tissue from the seed. As mentioned earlier, removed tissue can be collected for testing or analysis. Alternatively, testing or analysis of the remaining seed can be conducted as the tissue removal can be designed to expose or allow access to tissue in the remaining seed.

In the case of corn, a laser beam can be controlled to remove an area of the pericarp to gain non-destructive access to underlying seed tissue(s), part(s), or structure(s) of interest. As illustrated in the cross sections of a corn kernel in FIGS. 5A and B, two possibilities are the embryo 74 or the endosperm 76. The embryo 74 is usually at or near the tip cap end 67 of the seed and nearer one flat side of the seed than the other. The endosperm extends roughly along the entire opposite side from the embryo side, but broadens out and occupies most of the interior at the seed end opposite the tip cap. Thus, access to either embryo or endosperm is possible from one flattened side of the corn seed, without removal of much intervening seed tissue. In particular, either embryo or endosperm can be exposed by essentially removal of a small amount of the outer seed coat or pericarp.

By initialization and calibration, a laser can be controlled to remove only enough of the pericarp to gain sufficient internal access that an assay can be conducted on certain desired internal tissue or structure. The laser can also be controlled to remove only enough of the pericarp to gain sufficient access to the interior without materially affecting the viability or germination potential of the seed.

By empirical testing, the power and speed of the beam can be adjusted to meet those goals. As illustrated in FIGS. 8-14, the area removed is typically a fraction of the total area of one side of the kernel. A typical depth of ablation would be through the pericarp and then just enough to expose but not destroy the target internal tissue or structure. By appropriate set up, calibration, and empirical testing, operation of the laser can be non-destructive of the seed by controlling heat generated by the laser, removing only certain seed tissue, and removing only so much seed tissue to gain access to underlying tissue or structure of interest. Such operation is non-destructive in the sense that it does not usually materially reduce viability of the remaining seed or its germination potential. It has been found that a laser includes the benefits of high precision in control of movement, area and depth of ablation, and its efficiency.

However, other methods of non-destructive seed tissue removal are possible. One example is a water jet or abrasive jet (e.g., commercially available from Berkeley Chemical Research, Inc., Berkeley, Calif. 94706-026; Flow International Corporation, Kent, Wash. USA; and others). Another is a grinding tool (e.g., Dremel brand MultiPro™ rotary tool) with appropriate sized bit and tip (e.g., engraving, cutting, grinding, carving, sanding, or routing bit tip available at a variety of commercial locations or on-line from Robert Bosch Tool Corporation). Additional description and illustration of alternative tools or methods of removing tissue from seed are set forth in U.S. application Ser. No. 11/939,402, filed Nov. 13, 2007, which application is assigned to the owner of the present application and incorporated by reference herein in its entirety. The system of FIG. 18, also described in more detail in application Ser. No. 11/939,402, provides a specific example of removing tissue from a seed by cutting off a single piece of the seed. In the example of FIG. 18, the cutting tool is a laser.

4. Seed Specific Analysis (Step 206)

A number of analyses can be applied to the seed after tissue has been removed, or to the removed tissue from the seed. One example is genetic analysis. By methods known in the art, exposure of the embryo, for example, allows assays to be performed for detection of nucleic acids from which genetic information about the seed can be derived.

An example of one such method is as follows. The ablated seed can be immersed in a polymerase chain reaction (PCR) mixture in preparation for any number of PCR analyses. A detector can generate a signal representative of some aspect of the PCR from which genotyping can be derived. Details of such a signal and its use are well known. A variety of PCR detectors are commercially available. One example is an optical detector for PCR (e.g., Chromo4™ Real-Time PCR Detector from Bio-Rad Laboratories, Inc., Life Science Research Group, 2000 Alfred Nobel Drive, Hercules, Calif. 94547 USA).

Nucleotide sequences can be used to isolate corresponding sequences from other organisms, particularly other plants, more particularly other monocots. In this manner, methods such as PCR, hybridization, and the like can be used to identify such sequences, or fragments thereof, based on their sequence homology.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, inter alia, Innis et al., eds. (1990) PCR Protocols: A Guide to Methods and Applications (Academic Press, New York); Innis and Gelfand, eds. (1995) PCR Strategies (Academic Press, new York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers, and the like.

In hybridization techniques, all or part of the nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Methods for preparation of probes for hybridization and for construction of genomic libraries are generally known in the art.

To achieve specific hybridization under a variety of conditions, such probes include sequences that are unique and are generally at least about 10 nucleotides in length or at least about 20 nucleotides in length. Such probes may be used to amplify corresponding sequences from a chosen plant by PCR. This technique may be used to isolate additional coding sequences from a desired organism, or as a diagnostic assay to determine the presence of coding sequences in an organism. Hybridization techniques include hybridization screening of plated DNA libraries (either plaques or colonies).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing).

Another analysis could be cellular level analysis. An example with respect to corn is described at Gabriella Consonni et al., "Genetic Analysis as a Tool to Investigate the Molecular Mechanisms Underlying Seed Development in Maize", Annals of Botany 2005 96(3):353-362, which is incorporated by reference herein.

A still further example is nanoscale analysis. See, e.g., Georg H. H. et al., "Analysis of Detergent-Resistant Membranes in *Arabidopsis*. Evidence for Plasma Membrane Lipid", Plant Physiol. 2005 January; 137(1): 104-116, incorporated by reference herein.

Chemical analysis is another example. A variety of tests can be performed to, for example, identify a chemical trait of the tissue.

Other procedures or analyses are, of course, possible. The tissue removal step provides a sample for such analyses. One skilled in the art is familiar with the different analyses and testing that can be done on seed.

5. Selection From Candidate Seed (Step 211)

Once analysis has been completed, results or information from the analysis can be used to, for example, distinguish a seed from other seed, or identify a trait of the seed. This can be used to select one seed over another, or select a seed because of its trait. One example is a seed that, through genotyping, is indicated to be more drought-resistant than other genotypes. By effective non-destructive ablation of a seed with a laser (or other removal of seed tissue), and by an appropriate genotyping assay, a seed indicative of drought resistance genetic make-up can be identified.

As diagrammatically illustrated in FIG. 1, selection can be from a plurality of different candidate seed. The different candidate seed 1, 2, . . . n are identified and collected (step 202). A first sample seed 1 (step 203) is processed through steps 204, 205, and 206, and a result of or data from the test of step 206 is recorded (step 207). One or more other sample seed (e.g., sample(s) 2, 3, . . . n) are similarly processed (steps 204-206) and the test results stored for each (207) in correlation with their identifying information (202). This provides one basis for comparison between two or more of the samples (step 210) and subsequent selection between the two or more (step 211) of seed that is deemed desirable (e.g., for further research or commercial production). As indicated in FIG. 1, the comparison between samples can be based on any of variety of factors capable of analysis with seed specific tests of the samples.

Importantly, non-destructive tissue removal and analysis allows such identification to be made without either planting the seed and waiting to test a tissue sample from its growing plant or having to use the land or greenhouse space, labor, and supplies to plant and grow the seed into plants. The controlled, precise, non-destructive removal of seed tissue for testing, or to gain access to relevant underlying tissue or structure for testing, allows analysis to make selections based on tissue of the seed, not on a plant grown from the seed. As can be appreciated, this represents a potential substantial savings in time, labor, and resources, including land resources, for selection processes for seed companies. The controlled, precise non-destructive tissue removal is capable of substantial automation, thus improving through put and efficiency of plant selection processes.

With respect to corn seed, removal of at least exterior (pericarp) tissue is difficult. It was not considered practical or feasible to do so efficiently and/or non-destructively to the seed on a large scale. The pericarp 78 (FIGS. 5A and B) of corn seed is a relatively robust seed tissue (somewhat like a fingernail) and difficult to separate from underlying seed tissue structures. Any removal of a portion of the pericarp to expose tissue or structures inside the kernel is laborious and difficult. This is well-known in the art. A variety of methods have been attempted to remove pericarp. Some include chemical baths (steeping) or mechanical methods (e.g., grinding). These require careful workers and are time consuming. They also tend to be destructive of the seed.

An important reason to expose interior tissues of a corn seed is to gain access to male and female genetic material to assay and evaluate genetic content. This allows researchers the ability to know if a seed contains a gene of interest. If so, the seed is then identified as a candidate for further research or to produce commercial quantities of the seed. The method 200, controlled forces are used to remove specific seed tissue in a non-destructive manner. This, in turn, allows testing and analysis, seed selection, and then planting and germination of the selected seed for further use. One further use is development of commercial quantities of seed from the selected seed; such as a commercial seed product for seed companies.

But additionally or alternatively, removal of tissue from a seed provides a sample from the seed for testing. The method could be used to remove not only a portion of the pericarp but also a specific type and amount of interior tissue (e.g., endosperm or embryo). For example, controlled operation of a laser could ablate an area of the pericarp as well as a portion of the embryo lying immediately under the pericarp. The debris from the ablation (i.e. the removed tissue) can be collected and tested. The debris is essentially a sample of candidate seed. The testing of the debris is thus a testing of the seed. If controlled appropriately, the tissue could be removed by laser ablation in a manner non-destructive of the remaining seed, so that the remaining seed retains germination potential. However, this is not required. By removal of a small sample from the candidate seed, the sample could be immediately tested to allow rapid decisions to be made about the seed and its traits. Because the sampling and testing can be carried out on a single seed (which is non-destructive of the plant or other seed of the plant), the method can be not only rapid but provide relatively high throughput for plural candidate seed.

There are other beneficial applications for a methodology of processing seed to remove a certain relatively accurate amount of tissue from the seed. A variety of situations exist where removal of some portion of the seed is desired. The method described above utilizes steps to non-destructively remove desired seed tissues. Other uses for seed tissue or exposed seed tissue are well known in the art.

D. Specific Example 1

FIGS. 2-14

FIGS. 2-14 illustrate one specific approach to the method of FIG. 1. The tool or method of ablation to remove seed tissue is a laser. In this specific example, a specific seed holder is used for positioning a candidate seed relative to the laser.

Figure 2:
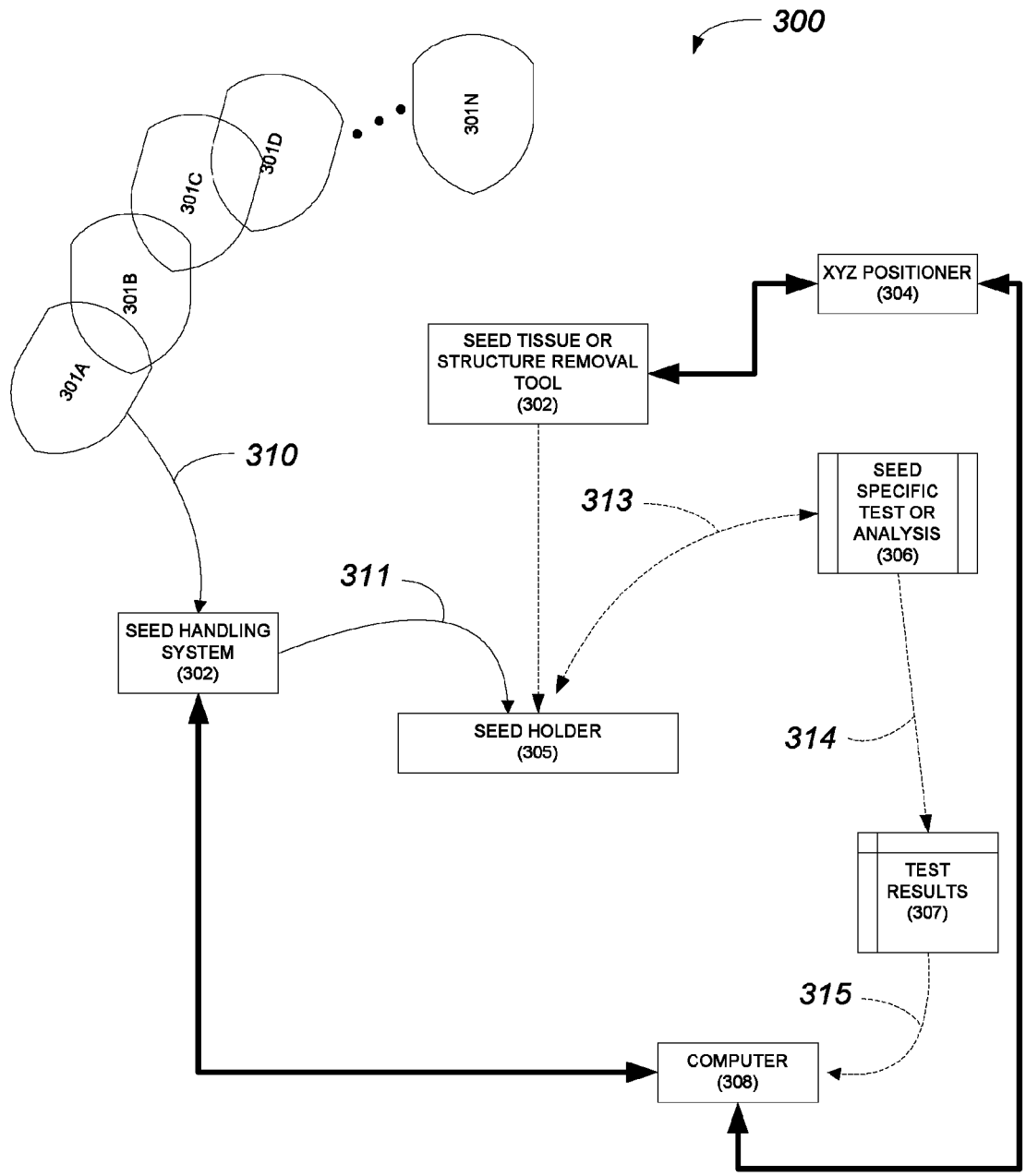
FIG. 2 is a block diagram illustrating apparatus and functionality relative to a first specific Example 1 of practicing the method of FIG. 1.

FIG. 2 sets forth diagrammatically a block diagram illustration of a system and apparatus 300 to practice method 200 of FIG. 1. Plural seed samples 301A-N are prepared and provided for processing and analysis to a seed handling system 302. Seed handling system 302 presents the samples 301 to a seed holder 305 which defines a testing location 320. A tissue removal tool 302 is controllable by positioner 304 to operate on a seed in the test position 320, specifically to remove a specified amount of seed tissue from a specified area of the seed. Once the tissue is removed, a seed specific test 306 is performed on the seed. As indicated, in this example, the test is performed at the testing location, which is the same location as the tissue removal step. This can save time and improve efficiency of throughput. Test results 307 are collected and can be recorded in computer memory 308, for example.

Reference numbers 310-315 show the general flow path of these samples and test results from the samples. Many of these functions can be substantially automated. This allows multiple sample seed to be processed with minimal manual steps, which can increase accuracy and efficiency.

FIG. 3 illustrates a laser ablation system 10 that could be used as the tissue removal tool to practice the exemplary method 200 and exemplary system 300 of FIGS. 1 and 2.

1. Tissue Removal Tool

In the system 10 illustrated in FIG. 3, a laser 16 is the tissue removal tool. One example is a Firestar™ f201 Series, Model # FSF201SB, water-cooled sealed carbon dioxide ($CO_2$), 200 watt laser commercially available from Synrad, Inc. of Mukiteo, Wash. (USA). Laser 16 has typical characteristics and adjustability (e.g., power or intensity).

A $CO_2$ type laser has proven efficiency, as well as reasonable cost and high power capability. It runs in the infrared wavelengths. It is widely used for cutting and welding, but is also frequently used for surgical procedures because the water in most biological tissue absorbs the $CO_2$ laser's frequency of the light. Other types of gas lasers could be used, as can other types of lasers (e.g., chemical, metal vapor, solid state (e.g., YAG) and semiconductor).

Laser 16 normally would include an optics package, such as beam delivery components (see reference numeral 130 at FIG. 8), to focus and control the laser beam. Conventional auxiliary equipment, such as power supply, control circuit, and the like, would also be used. Such optics and accessories are typically available from the laser vendor or manufacturer, as they are from Synrad. With the FSF201SB laser identified above, a beam delivery system is used that transfers the raw laser beam from the sealed laser and focuses it at the location to cut the seed (e.g., the testing location). An example of an optic system is a Haas Laser Technologies Inc. 1.25" series beam delivery system with a 5" focal lens. Any of the typical types of laser cutting systems could be used, including flying optics, hybrid, and pivot-beam, to precisely control movement of the laser beam relative to its target application.

By empirical testing and calibration, laser 16 can be set to ablate a pattern or area of one side of a seed to a relatively controllable depth. Following the manufacturer's set up instructions, laser 16 can be configured to produce laser beam 132 of a certain width, power, modulation, and color designed for desired ablation of a surface of a corn kernel to remove an area of pericarp and provide access to tissues underneath the pericarp, and to do so non-destructively.

It is to be understood that lasers can be controlled so accurately and minutely that it is possible, if desired, to etch a marking, letters, or numbers on the surface of seed kernel, if desirable. One use would be to mark an identification of the seed sample directly on the seed.

For adequate control of position, size, and depth of tissue removal of corn seed, the tissue removal tool ideally should have a pre-determined spatial resolution. The ablation can be varied across a seed. It could be varied from seed to seed across plate 18. It could be varied in amount (e.g., area and volume) of tissue removed, position of tissue removed, or which tissue is removed (e.g., pericarp, endosperm, and/or embryo). If the objective is exposure to cells for genetic testing, the laser ablation can open up the interior of specific tissue, parts, or structures of the seed. In one example, the ablated seed can then be placed into a solution (or a solution added to the well 40 in which a seed is ablated) to extract DNA, and then analyze it. The solution and DNA extraction methods are well-known to those skilled in the art.

It is to be understood that it may be possible that other forms of energy or forces could be used for the removal of tissue or structure from seed. Some examples have been mentioned previously.

In this example of laser ablation, set up and application of laser energy as the mode of ablation is akin to laser ablation in medical, usually surgery, or biological applications. Seed is similar to human soft tissue, inter alia, because it is biological and contains a significant amount of water.

The process is greatly affected by the nature of the material and its ability to absorb energy. Therefore, the wavelength of the ablation laser should have a minimum absorption depth. While these lasers can average a low power, they can offer peak intensity and fluence given by:

$$\text{Intensity}(W/cm^2) = \text{average power}(W)/\text{focal spot area}(cm^2)$$

$$\text{Peak intensity}(W/cm^2) = \text{peak power}(W)/\text{focal spot area}(cm^2)$$

$$\text{Fluence}(J/cm^2) = \text{laser pulse energy}(J)/\text{focal spot area}(cm^2)$$

while peak power is $$\text{Peak power}(W) = \text{pulse energy}(J)/\text{pulse duration}(s).$$

Laser ablation of seed is similar to laser soft tissue surgery. Interaction of a highly focused laser light beam with soft tissue basically vaporizes the soft tissue with high water content. Such a laser can make a very small incision. $CO_2$ laser wavelengths (e.g., 10,600 nm) are highly absorbed by water-containing biological tissues. They also tend to be less costly than solid state Er:YAG lasers, which also feature a wavelength that is highly absorbed by water.

Ablation of a seed is performed similarly to the surface ablation of the cornea for several types of eye refractive surgery (e.g., LASIK and LASEK). Material is removed from the solid by irradiating it with a focused laser beam. At low laser flux, the material is heated by the absorbed laser energy and evaporates or sublimates. At high laser flux, the material is typically converted to plasma. Usually, laser ablation refers to removing material with a pulsed laser, but it is possible to ablate material with a continuous wave laser beam if the laser intensity is high enough.

The depth over which the laser energy is absorbed, and thus the amount of material removed by a single laser pulse, depends on the material's optical properties and the laser wavelength. Laser pulses can vary over a very wide range of duration (millisecond to femtoseconds) and fluxes, and can be precisely controlled.

Types of laser setups can include, but are not limited to, moving material, hybrid, and flying options systems. Moving material has a stationary cutting head and moves the material under it. It requires fewer optics, but requires moving the work piece or material being ablated. Hybrid lasers provide a table which moves in one axis and moves the head along the shorter axis. Flying optics feature a stationary table and a cutting head (with laser beam) that moves over the work piece in both of the horizontal dimensions. Another example of beam movement is by a rotating or vibrating mirror. The mirror moves in a manner which may trace out the desired pattern on the surface.

The point where the laser touches the surface should be on the focal plane of the laser's optical system and is usually synonymous with its focal point. This point is typically small (e.g., less than a fraction of a millimeter depending on wavelength). Only the area inside this focal point is significantly affected when the laser beam passes over the surface. The energy delivered by the laser changes the surface of the material under the focal point. It may heat up the surface and subsequently vaporize the material, or perhaps the material may fracture (known as "glass" or "glass up") and flake off the surface. This is how material is removed.

Different patterns can be engraved on objects such as seed by programming a controller to traverse a particular pattern for the laser beam over time. The trace of the beam is carefully regulated to achieve a consistent removal depth of material. Criss-cross paths are avoided. The speed of beam movement is also considered. Changing the intensity and spread of the beam allows more flexibility. For example, by changing the proportion of time (known as "duty-cycle") of the laser is turned on during each pulse, the power delivered to the surface can be controlled appropriately for the material.

As can be appreciated by those skilled in the art, the following are factors in controlling laser operation:

(a) speed of motors moving the laser beam relative the seed;

(b) wattage of the laser (usually a defined amount, e.g., 75 watts), (c) frequency of the laser (controls heat generated when the laser hits the seed).

Also, other operations can affect laser sampling. One would be use of compressed air (e.g., 30 psi) to remove debris from the area where the laser is striking. Vacuum is an alternative.

Ventilation through blowers or a vacuum pump can be used to remove the fumes and smoke arising from this process, and for removal of debris on the seed surface to allow the laser to continue essentially engraving the material.

2. Seed Holder

Each seed can be held in position for tissue removal by the tissue removal tool. One example is a container including a well or cavity defined by a sidewall between a bottom and open top. FIGS. 3 and 4A-D illustrate a multiple well container or plate 18 having a plurality (ninety six) of wells 40 arranged in an indexed matrix of rows and columns (eight rows A-H and twelve columns 1-12). Each well position can be indexed by row/column (e.g., A/1, A/2, ... H11, H12). In this manner, identifying information about a seed in a well can be recorded relative to the particular well in which it is placed to maintain a correlation between each seed in plate 18 and its identity. As illustrated in FIG. 4A, in this example wells 40 are equally spaced apart on top 42 of plate 18. The ninety-six wells 40 correspond with a conventional number of seed or samples used in plant breeding assays or many laboratory tests.

Plate 18 can be of any of a variety of materials and configurations. Its primary functions are to hold each seed in a static position relative to the tissue removal tool and in isolation from other seed so there is no co-mingling between seed.

One example of plate 18 has the following characteristics. It is solid metal with machined wells 40 of cylindrical shape. Examples of metal include but are not limited to aluminum, steel, or brass, or alloys thereof. Others are possible. Alternatively, plastics could be used. An example of plastic is acrylic. Other materials are possible. Examples are rubber or metal foil. The material should be compatible with the tissue removal tool and its forces.

An example of aluminum would be raw aluminum, 6061 grade. The sidewall and bottom of each well could be configured to absorb laser light, reduce reflections, and/or cause diffusive reflection of the laser light, if a laser beam tissue removal tool is used. For metals or alloys of metal, those surfaces could be powder-coated, anodized, sandblasted, painted, or otherwise textured or configured to reduce reflections or be substantially light diffusive.

In the example of plate 18, it is designed to contain a single seed per well. Each well has a specific design element which aids in centering the seed in the well (e.g., conical bottom as discussed below). The well is also powder coated with a substance which minimizes laser reflections or is light diffusive. An example is Alesta™ brand powder coating, from DuPont of Wilmington, Del. USA. Sandblasting and anodization are other methods of altering a surface, especially aluminum, to make it less specular and more diffusive. Other ways are possible.

For plastics, the material itself can be light absorbing or light diffusive, or a reflection-deterring texturing could be machined or molded into the plastic. Another method of reducing reflections is to alter the geometry of the bottom and/or sidewall defining a well. Angling the surfaces of those portions can assist in deterring unwanted reflections of a laser beam out the open top of the well.

By using individual wells for each individual seed, singulation and isolation of each seed from other seed is automatically achieved. Each well 40 is a cylindrical bowl with a conical countersunk bottom 58.

Positioning and orientation of the seed can be accomplished in a variety of ways. With respect to plate 18, each well 40 is made wider than the longest dimension of a kernel 60 but has a conical, countersunk floor 58. This assists in centering the corn seed 60 in well 40. The shape and internal contents of a typical corn seed are illustrated by FIGS. 5A and B. Note how the embryo 74 is near the tip cap end 66 of the seed, and near one flattened side face 62. The endosperm 76 occupies much of side and end opposite the tip cap 62. It has been found that the conical countersink of floor or bottom 58 of well 40 helps automatically center a corn seed (or any seed or particle) in well 40. Also by appropriate diameter, well 40 and conical countersink tend to position a corn seed with its flattened faces generally parallel to a plane across the bottom of well 40. This allows one of the largest surface area sides of the corn seed to be exposed to the top of well 40. The laser can be set for any depth for each well (see plane D in FIG. 8). By initialization and empirical testing, an average depth for a particle set of seed samples can be established. This avoids having to adjust the depth of cut for each seed. It has been found to work well for most corn seed. However, depth of cut, as well as area of ablation can be controlled differently for each seed sample, or they can be adjusted for different types of seed, or different varieties of seed, if needed, as average seed size can vary. As can be appreciated, the laser can make multiple scans across the same locations of the seed to incrementally remove tissue until a certain final depth. Alternatively, one scan is used to cut to the final depth. Empirical testing can establish the desired process.

FIG. 6A illustrates an alternative example of a seed holder. A blister pack type member 100 has a base sheet or substrate with multiple holes from which plastic bubble-shaped clear plastic containers 102 extend. Further detail can be found at U.S. patent application Ser. Nos. 12/235,100, filed Sep. 26, 2007, and 12/545,283 filed Aug. 21, 2009, which applications are assigned to the owner of the present application and incorporated by reference herein in their entirety. Containers or bubbles 102 are analogous to wells 40 of plate 18. Each bubble would receive, singulate, and isolate a seed from other seed. A release sheet can be removably adhered or attached over the top of the holes in substrate 100 to seal the contents of the bubbles 102, if desired. FIG. 6A shows blister pack 100 configured to have an identical number and spacing of bubbles 102 relative to number and spacing of wells 40 of plate 18. Blister pack 100 could be used to store candidate seed samples in an indexed fashion (8 rows×12 columns) with a release sheet over bubbles 102. Those 96 samples could be easily transferred to the 96 wells of plate 18 by removing the release sheet from blister pack 100, inverting plate 18 with empty wells over blister pack 100 with wells 40 and bubbles 102 aligned, and then inverting both blister pack 100 and plate 18 to transfer seed from blister pack 100 to plate 18. But, an alternative use of blister pack 100 could be as a substitute for plate 18. Blister pack 100 can be placed with the holes facing up and without any release sheet over them. Individual seed kernels can be placed into each bubble. The tissue removal tool can then be manipulated, as described with respect to plate 18, to move to and operate on a seed in a first bubble 102, then move to the next seed and bubble, and so on.

Other seed holders are possible. For example, a pedestal or pin with a head adapted with a receiver or cradle might be used to hold a single seed, isolated from other seed, in a manner that can be presented to and operated upon by a tissue removing tool. Tubes in racks or press and seal containers are other examples of devices that can isolate and hold individual seed in a position for tissue removal.

FIG. 18 illustrates an example of an alternative seed holder. In system 150, a wheel 154 turns in synchronization with a seed filler device 152. Wheel 154 has multiple magnets 156A-F equally spaced apart around its perimeter. Each seed 60 has been previously painted or dipped in magnetic or iron-based paint 158. In synchronicity and generally concurrently, a seed 60B drops from seed filler 152. Prior dropped seed 60C, bound to magnet 156C by magnetic attraction of iron-based paint 158 to magnet 156C, rotates towards laser beam 132 of laser 16. Seed 60D is at the testing position and has tissue removed by laser beam 132. Processed seed 60E moves toward scraper 162. Seed 60F is knocked from its magnet 156F by scraper 162. Thus, system 150 similarly singulates and isolates single seed from one another, and uses a tissue removal tool. Furthermore, even though without a container such as a well or bubble, each seed is positioned rather uniformly. In fact, by placing the magnetic paint 158 (e.g., magnetic primer paint commercially available from Rust-oleum of 11 Hawthorn Parkway, Vernon Hills, Ill. 60061 USA, or magnetic wall paint from Kling Magnetics, PO Box 348 343 Rt. 295-Chatham, N.Y. 12037 USA) in the same position on each seed 60 (here on its crown), system 150 generally uniformly positions each seed. It can more uniformly and automatically orient each seed 60 in the same general orientation to laser beam 132. Further details about a system like system 150 can be found in U.S. application Ser. No. 11/939,402, filed Nov. 13, 2007, which application is assigned to the owner of the present application and incorporated by reference herein. The incorporated-by-reference application discloses utilization of a metal or ferromagnetic material applied to a portion of the exterior of a seed. The seed can then be automatically attracted to a magnetic field (of a permanent magnet or electromagnet). Depending on the position of the magnetic paint on the seed, the seed can automatically be positioned in a predetermined orientation. This would allow the combination to be used to position and hold a seed relative to a tissue removal tool.

System 150 can also use an automated seed filler or motion system to move seed filler chute 110B in an orderly fashion so that seed 60, after laser processing, are placed in individual wells or bubbles in a tray or bubble pack 100B (see illustration of how seed 60A-F would end up serially deposited in row and column form). Alternatively, an automated motorized positioner or motion controller could move tray 100B relative to chute 110B in such an orderly fashion.

Seed fillers or other similar seed or particle handling components that can be programmed and automated are available from a variety of vendors including Elmor™ products from Elmor Angewandt Elektronik of Mangelegg 58 CH-6430 Schwyz, Switzerland. Such machines can drop one seed at a time, or fill multiwell containers serially, like a multiwell plate 18 or a multi-bubble blister or bubble pack. Other types of small particle handlers or conveyors could be used to move, singulate, transfer, or otherwise handle individual seed. Another source for such machines are fillers and packagers, including for seed, from Visser International Trade & Engineering B.V., P.O. box 5103, 3295 ZG's-Gravendeel, The Netherlands.

Although system 150 in FIG. 18 illustrates using a laser to cut off a clip or part of each seed, by appropriate setup and control, system 150 could be used to ablate or remove just a small amount of surface tissue, as described with respect to system 10. This would likely require that wheel 154 be stopped at least momentarily when a seed 60 is in the laser beam path, and the laser beam 132 raster scanned across a side of seed 60.

3. Automated Handling

Commercially available equipment can be used to automate or semi-automate many of the functions of system 10. Examples are as follows.

As indicated in FIG. 3, plate or other seed holder 18 can be positioned on base 12 in the field of movement of laser 16. In this example, plate 18 contains ninety-six spaced apart wells 40 sized to each receive a single corn kernel 60.

It has been found that processing of a plurality of seed (here 96) can be done relatively rapidly in an automated fashion with system 10. However, since ablation of the seed is with laser energy, is not trivial as to how to present each seed to the laser beam. Similarly, complexities exist with other forces that might be used for tissue removal (e.g., water jet, grinding).

A base 12 (platform, table, or the like) supports a frame 14 which in turn supports an automated tissue removal tool. In FIG. 3, the tool is laser 16 that is programmably movable via an XYZ positioner system 20 or other motorized positioning devices or systems.

Any of a variety of commercially available motorized positioners could be utilized. FIG. 3 diagrammatically illustrates that a moveable rail 22 can move along the top of frame 14 by a computer-controlled motor 24. A carriage 26 can move across rail 22 by computer controlled motor 28. Laser 16 can move up and down relative to the top surface of plate 18 on carriage 30, which is computer controlled through motor 32. Carriage 30 moves on an arm that is attached to carriage 26. As indicated in FIG. 3, this allows multiple degrees of freedom of movement of laser 16 relative to plate 18. The ways in which the three dimensional movement of the tissue removal tool occurs relative to the seed holder can vary. It is possible that the seed holder could be moved relative to the laser, or both moved relative to each other.

A controller 36, such as are commercially available, can be in communication with a computer 38. Computer 38 includes software that allows the user to program movement of XYZ positioner 20, and thus laser 16, relative to each well 40 in plate 18. Controller 36 would execute on that program through some sort of power supply in junction box 34 that would control motors 24, 28, and 32 to very accurately position laser 16 and its beam 32, and move the beam across a seed. In this way, an automated laser ablation of a single seed in each well 40 of the 96 well tray 18 can be accomplished without manual labor or control.

Examples of positioner systems with programmable control are available from Synrad and made by such companies as Techno Inc. of New Hyde Park, N.Y. USA; Anorad Corp. of Shirley, N.Y. USA; and Aerotech, Inc. of Pittsburgh, Pa. USA.

Examples of other automation would include a seed filler, as previously discussed. It could be used to move a single seed and drop it in a specified well, bubble, or designated location of a seed holder.

Furthermore, equipment can be used to move seed from a well, bubble or other location to a designated location after the tissue has been removed. An example would be to utilize magnetic tape or other magnetic coating or attachment to each seed 60, as described above with respect to FIG. 18 to allow automated movement of each seed between locations. An electromagnet or other magnetized subject could be used to pick up individual seed 60 from a batch of seed 60, move those individualized seed into position over individual wells 40, and then deposit them in wells 40. By reverse process, after ablation, the system could grab the seed out of each well and move them to another station. A still further alternative would be vacuum systems, such as can be developed with the skill of the ordinary artisan, and could be used to pull seed from a batch, singulate them, deposit them in wells 40, and then remove them at an appropriate time.

Further, the seed holders such as plate 18 or blister pack 100, or other seed holders that have a well or cavity, could be used for additional functions over and above singulating, isolating, and holding a seed for operation by a tissue removal tool. Well 40, bubble 102, or the like could also function as an assay vessel. One example is that a liquid mixture for polymerase chain reaction (PCR) could be placed directly into well 40 or bubble 102 after tissue removal. The reaction could occur and be analyzed for any of a wide variety of data such as is well known by those skilled in the art. This avoids having to move and keep track of identification of multiple seed. Such in situ seed specific analysis can occur efficiently and with relatively high throughput of multiple samples. Results of the analysis can be recorded (e.g., in a database or otherwise) with correlation to the identity of each seed. Those results can then be used in a number of ways.

Automated liquid handling equipment could also be used to move liquid or liquid mixtures or suspensions in a controlled, preprogrammed manner. An example is the liquid PCR assay described above. Liquid may be used, for example, for other testing of the seed after tissue removal. Such liquid handling equipment is commercially available and widely used in laboratory settings. Examples are automated liquid handling systems from PerkinElmer Life And Analytical Sciences, Inc., 940 Winter Street, Waltham, Mass. 02451 USA.

As indicated in FIG. 3, a computer 38 can be used to not only facilitate programming of the automated handling equipment, but also can be used to record and store information about the tissue removal and/or any seed specific analysis performed on the seed.

Other handling components could include a sub-system for keeping track of identity of the samples or sets of samples. Bar codes or other machine-readable labels or tags (e.g., RF tags) could be mounted on any of the containers, carriers, trays, or plates that include seed. This would allow maintenance of correlation of samples to original identifying information.

4. Operation

For efficient, high throughput operation of system 10 of FIG. 3, individual kernels 60 are deposited in each well 40 of plate 18. FIG. 6A illustrates one possible way to do so. A blister pack 100, having 96 clear plastic bubbles 102, can contain seed of known origin or identity. A peel-off adhesive cover (not shown) can contain the seed in each of the bubbles 102, even when blister pack 100 is inverted. Blister pack 100 can be brought to ablation plate 18, the peel off cover removed, and plate 18 inverted and placed so that each of wells 40 is in alignment with a bubble 102. The combination of bubble pack 100 and plate 18 can be turned over and each of the 96 seed from bubble pack 100 would fall into a corresponding well 40 and plate 18. Plate 18 could then be placed in a referenced position on base 12. After ablation, the reverse procedure could be used to place seed back into the bubbles 102 of bubble pack 100 for transportation to a next step if desired.

FIG. 6B shows an alternative system. A seed tube 110 could be in communication with a seed singulator 112. The combination could deliver a single seed down tube 110 that could be aligned with a well 40. Tube 110 could be moved to the next well 40 and the next single seed delivered, and so on. Tray or seed fillers are commercially available. Examples have been given earlier.

There are other ways to place seed in wells 40. One is simply to manually place a seed in each well 40. This may be preferable in that the user can ensure that the seed is centered in well 40 and that a flat wide side of the corn kernel is basically facing up relative to the open top into well 40. As previously mentioned, plate 18 can be intentionally manufactured to have a conical bottom 58 for each well 40 to assist in centering kernel 60 in well 40, as the geometry of such a well encourages the corn seed to lie in a manner where a wide, flat side is facing up.

Once a single seed 60 is in each well 40, and plate 18 is in its reference position on base 12 of system 10, controller 36 would begin the ablation process with laser 16 to remove specific tissue from the seed.

As is illustrated in FIG. 7, controller 36 could include software on PC 38 which allows the user to design the specific ablation pattern for each well 40. A computer display 124 on PC 38 could show the center of each well 40. The user could designate or design the specific ablation pattern in relation to well 40. As shown in FIG. 7, the pattern can be rectangular in the horizontal plane (see reference numeral 122). The dimensions of rectangular pattern 122 can be selected and can even be displayed on computer screen 124. The user could also select power level, color, modulation, and other relevant operational parameters to control how that rectangular shape is ablated, cut, etched, or otherwise formed in each seed, as well as the depth.

As can be appreciated, a wide variety of patterns are possible with laser 16. FIGS. 8A and B and 9A-C illustrate one example of a possible shape.

In this example, laser 16 is configured with optics 130 to create a laser beam 132 that has a 0.0005 cutting width (at ¼ inch focal length). The dimension of shape 122 is 0.2 inch square. As illustrated in FIG. 8B, controller 36 is programmed so that laser beam 132 scans back and forth on the surface of kernel 60 to ablate or remove tissue to make that shape. As indicated in FIG. 8B, the beam would cut a first swath 92A of 0.0005 from one side of shape 122 to the other. It would then go back along a slightly different path (reference number 96B). It would scan back and forth progressively etching or ablating additional material but keeping the rectangular shape 122 until a final depth is reached. FIG. 8B illustrates linear paths 92A through 92H. In practice, there would be on the order of 30 to 40 scans to complete the cutting out of cavity 80 in the programmed shape 122 of FIG. 7.

In this example, just enough tissue is ablated to expose underlying relevant tissue or structure in the corn kernel. By scanning the laser beam in a relatively rapid manner, ablation of the seed tissue is accomplished without excessive heating or other conditions which materially adversely affect germination viability. Automated system 10 could allow ninety six different seed to be sequentially ablated in this manner without any manual human steps.

FIG. 8A illustrates diagrammatically and not to scale the cavity 80 of a rectangular prism shape. Laser ablates material from seed 60 in that shape to remove the outer pericarp and expose interior tissues. This could be endosperm. It could be the embryo. In any case, the process can be configured to not materially affect viability for germination of corn seed 60. FIGS. 9B and 9C show alternative views of cavity 80 created by laser 16 for that seed.

It is to be understood that the exact manner in which laser 16 creates cavity 80 can vary. Beam 132 can be moved back and forth with an XYZ positioner such as indicated in FIG. 1. Alternatively, there could be optical methods to change the angle of beam 132 or create back and forth scanning cutting action of the beam.

Once laser ablation of a seed 60 in well 40 at the reference A1 position of plate 18 (see FIG. 4A) is completed, laser 16 would be moved by controller 36 to a referenced position over well 40 at position A2 of plate 18 and the laser ablation process to etch shape 122 for that well and seed would be conducted. Once completed, laser 16 would move to position A3 and so on until completion of row 1. It would then begin on the next row and continue until all 96 positions were completed.

It can be appreciated that the goal is usually to remove enough material to gain reasonable access to a specific interior tissue(s) of seed 60. For these purposes it is not essential that the area ablated is absolutely centered on a side of seed 60 or that it be precisely to a certain depth. By empirical testing and adjustment, and relative consistent positioning of a seed 60 in each well 40 (that is, as consistent as possible positioning in the center of the well 40), programming the laser to cut a shape 122 centered with the center of well 40 usually results in ablation of enough material to gain reasonable exposure to the desired interior tissues.

Programming of the shapes 122 is non-complex in many systems. Commercial systems usually allow the shape to be selected and displayed in a print file which is then communicated to the controller 36. An appropriate template or graphic user interface (GUI) at PC 38 or controller 36 allows adjustment of shape, area, and depth of cavity 40.

FIGS. 10A-C through FIGS. 14A-C are included just to give a few additional examples of how the shapes and depths of the ablation can be varied. As illustrated in FIGS. 10A-C, a first larger rectangular prism cavity near the top of the surface of seed 60 could be created to a first depth. A smaller area rectangular prism shape could then be etched to a lower depth. A third, still smaller rectangular prism could be etched to a still lower depth. This creates a stair step type cavity 80B. FIGS. 11A-C show that two rectangular channels could be etched in the seed, a smaller spaced apart from and inside a larger one. FIGS. 12A-C illustrate removal of a rectangular area over the embryo. FIGS. 13A-C and 14A-C show the patterns could be other than rectangular, e.g., more circular. More complex shapes are, of course, possible.

The high flexibility of the laser beam can make an almost unlimited number of shapes and depths of cavities. These shapes also can be designed to non-destructively remove tissue to expose underlying seed tissue of interest. Because the laser can have such a relatively narrow beam width, the system allows very accurate and minute positioning of the beam relative to the particle or item being ablated. Raster scanning of the beam allows progressive and precise control of final depth of cut. Optionally, the beam can be directed to a very specific portion of the item or seed. For example, laser ablation could be programmed for corn kernels to remove tissue just at or near the tip cap at one end or just near the other end or somewhere in between. Vector-based laser beam control is also possible. Vector-based movement follows the line and curve of a pattern.

Once all 96 seed have been ablated, they are ready for tests, as desired, to obtain information about the seed. For example, a variety of genetic testing procedures or assays could be used to identify the genetic material present in the seed. By that direct testing of a seed, a plant researcher could thus make a rapid determination if the seed is desirable for continued use in a plant advancement or breeding experiment, or for commercial production.

Removal of specific portion(s) of seed tissue(s), or use of exposed portions of the remaining seed portion(s), can be utilized for specific laboratory assays, which may include direct DNA, RNA, lipid, or protein isolations. Thus, this embodiment can be utilized in plant breeding processes in which identification of seed with desired traits or characteristics for subsequent germination to maturity in the field of green house can be relatively rapidly acquired directly from the seed. Examples of genetic analysis testing are set forth in U.S. Pat. Nos. 6,472,185, and 6,368,806 which are incorporated by reference herein.

As is well-known in the art, the identity of each seed, as well as its history, can be known and maintained throughout this process by a variety of techniques. For example, in the blister pack example, FIG. 6A, a bar code 108 or other machine readable label could be applied to blister pack 100 which identifies the origin and essential information about the seed in the blister pack on a well-by-well basis using the row and column indexing letters/numbers. By maintaining each seed in its corresponding column and row position in the blister pack, in plate 18, and back into blister pack 100 or into some other 96 well tray, the identity of each seed can be maintained. This would allow seed identified with the gene of interest to be known and their identity maintained by recording the position in the 96 positions of the array.

E. Specific Example 2

FIGS. 15-17

Instead of, or in some cases in addition to, removing tissue to gain access to the interior of a candidate seed, the removed tissue (or a portion thereof) can be collected and tested or analyzed. The test(s) or analysis(es) could be used to make selection decisions.

FIG. 15 shows in diagrammatic form a specific example. It is similar to FIG. 1 but with the following major differences.

The method 400 of FIG. 15 utilizes some tissue removal tool or method 402 to remove specific tissue from a candidate seed 401A. Seed 401A can be positioned in some holder component or position 405. The removed tissue (or a portion thereof) is collected in a collection container 403. Seed specific analysis is conducted of the collected removed tissue (reference number 406. The results are used (step 407) to make decisions (e.g., selection or not of the type of seed 401A for further use). Optionally, the test results and/or decision(s) can be stored or used by a computer 408.

It is to be understood that either Example 1 or 2 could be at least partially automated. But also, either Example could lend itself to rapid, local sample collection and analysis. For instance, a portable laser assembly could be taken to an experimental growing plot. Candidate seed from a growing corn plant could be removed, placed in a single well 40 and laser ablated. An appropriate solution could be added to the ablated seed in the well 40, DNA extracted into the solution, and the solution removed and genetically or otherwise evaluated. Or, the tissue removed by laser ablation could be placed in an appropriate solution or other assay and genetically otherwise evaluated. The evaluations could be used to make growing site decisions about the plant from which the candidate seed was taken. This avoids taking samples back to a remote laboratory and the overhead of transport and keeping track of which plant associates with which seed.

FIGS. 16 and 17 illustrate one example of how tissue removed from a candidate seed can be collected for analysis. Seed 70 is ablated by a laser 16 such as discussed in Example 1. A plume of fines or small particles (which act like smoke in the sense that they tend to float in the air) created by laser ablation would separate from seed 60. Sometimes they reformulate and coat the sides of well 40. This requires cleaning of plate 18 after each ablation process. A vacuum hood or head 140 (e.g., clear plastic) could be mounted on the optics or laser 16. It could be lowered with laser 16 over a well 40 during ablation of seed 60 in well 40. By utilizing vacuum hood 140 in operative communication through vacuum tube 144 to vacuum 142, those fines can be substantially, if not all, removed to eliminate this issue.

Alternatively, collection of the fine particles via vacuum or otherwise, can result in collection of enough material for testing, instead of testing the seed. This would require that the laser ablate tissue of interest for the test. For example, if just pericarp is desired for testing, the laser could be controlled to just ablate pericarp. The removed pericarp particles could be collected by vacuum and then tested. On the other hand, if endosperm was desired for testing, the laser could ablate the pericarp, the removed pericarp particles could be ignored or removed, and then the laser could ablate exposed endosperm, which could be collected into a container by, e.g., vacuum. Embryo tissue could be collected by removing pericarp over the embryo, then laser ablating the exposed embryo and vacuum-collecting the embryo particles.

FIG. 16 illustrates in simplified form laser ablation and vacuum collection from a single candidate seed. A seal or gasket 141 would seal hood 140 to the surface surrounding well 40 holding seed 70. Laser 16 would be operated to cause laser beam 132 to ablate seed 70. Vacuum source 142 (e.g., a vacuum pump) would be operated to cause fine particles to move from well 40 into container 146, but leave seed 70 in place. Container 146 could be removed and the collected particles from seed 70 tested.

Examples of vacuum systems include a variety of commercially-available particle filtration systems or fume handlers that could remove and/or collect the fines or collect. Particle extraction equipment is commercially available from companies such as AER of Old Saybrook, Conn. USA and Fumex of Kennesaw, Va. USA. This equipment is typically used in industrial air filtration/air pollution control systems for mist, dust, smoke, fume & gas/vapor contaminants in individual or combined forms. The system can include cartridge and bag dust/fume collectors, wet dust collectors, electrostatic precipitators, media filtration systems, and other components.

FIG. 17 illustrates that a tray with multiple wells 40 could be used with the vacuum extraction laser ablation system of FIG. 16. This would lend itself to efficient vacuum collection of removed ablated tissue from a plurality of candidate seed.

An alternative to vacuum collection would be to add a gel substance to each well 40. The gel would be transmissive of the laser beam. Fines resulting from laser ablation would tend to be collected by and suspended in the gel. The laser may have to be adjusted (which could be accomplished by empirical testing) to use a deeper cutting power if gel is used. It is possible that the fines collected in the gel could be extracted, collected, and assayed. To generate sufficient quantities of fines for some tests, the laser or other tissue removal tool may have to remove more tissue than if just removing enough to expose interior tissue.

F. Options and Alternatives

It will be appreciated that the present invention can take many forms and embodiments. The embodiments described in detail herein are by way of example only and not by limitation. Variations obvious to those skilled in the art would be included within the invention. However, a few additional examples of options, alternatives and variations, are provided below.

1. Types of Seed

The system and method described above can be applied to seed other than corn seed in analogous ways. Adjustments may be needed, as are within the skill of those skilled in the art.

2. Types of Tissue Removal Tools

As discussed previously, tissue removal from candidate seed can be accomplished by different methods or components (collectively referred to as "tools"). A laser is one such tool. It can be used in one mode to create small particles. In another mode is can be used to cut off a piece of a seed (see, e.g., FIG. 18 and associated description of a similar configuration shown and described in application Ser. No. 11/939, 402, filed Nov. 13, 2007, which application is assigned to the owner of the present application and incorporated by reference herein in its entirety.

Other tissue removal tools have been mentioned previously. application Ser. No. 11/939,402 includes additional details and examples.

3. Types of Analysis on the Seed

Various assays can be performed on the seed. Some examples have been given previously. One example is that an assay solution could be placed directly in wells 40 after seed 60 are ablated or tissue removed or exposed. The solution can be extracted and tests run to identify genetic material of interest. The wells can be drained and the seed moved to a carrier or package in preparation for further use. Alternatively, seed identified as having a gene of interest could be removed from their correlated position in the array of plate 18 and the remaining seed discarded. Another alternative is, after ablation, to move seed 60 to another container where an assay could be conducted. Additional types of testing can include, but is not limited to, genetic, physical, or chemical analysis on a cellular, molecular, or nanoscale level. Some non-limiting examples are:
   a. Spectroscopic;
   b. Genetic;
   c. Various nucleotide extractions and fingerprinting (e.g., DNA, RNA isolation);
   d. Protein and lipids isolation;
   e. Phenotyping;
   f. Trait or characteristic identification;
   g. Genetic marker assisted identification and selection;
   h. High throughput screening.

Those skilled in the art are familiar with the types of analyses that can be conducted on biological tissue, and which may be desirable or needed in making research and development decisions, as well as commercial production decisions, for seed.

A few examples of genetic analysis tests are as follows. Markers corresponding to genetic polymorphisms between members of a population can be detected by methods well established in the art. These include, e.g., PCR-based sequence specific amplification methods, detection of restriction fragment length polymorphisms (RFLP), detection of isozyme markers, detection of allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Others exist. Varieties of analysis for physical or chemical traits also exist and can be used.

Just a few methods of seed or seed tissue analysis have been mentioned. Others are known to those skilled in the art. A sample portion of a seed can be analyzed, or the remainder of the seed from which the sample is taken. The sample can be a single piece or multiple pieces. It can even be plural small particles. An example is what might be called debris that is generated, for example, when laser ablating a seed. As discussed, the debris scatters in small particles and can be like a plume of dust or smoke. It can be collected for analysis. Real-time fluorescence analysis is an example to detect the presence of certain genes. Another example of collection of seed debris from laser ablation is to use a tape with adhesive side above and facing the seed. The laser could pass through or around the tape, ablate the seed, and cause a plume of debris to rise. The debris would stick to the tape. Real-time fluorescence analysis could be used to analyze the debris on the tape.

Another option is to analyze the seed which has been ablated. For example, laser ablation could remove debris to leave a seed with a cavity (see, e.g., FIGS. 12A-C). An appropriate solution could be added to cavity to exact genetic material from the seed into a solution. The solution could be analyzed, e.g., for an indication of the presence of a gene or genes.
   a. Types of Application of Analysis of the Seed
   Examples of applications of the tests include but are not limited to such things as
   a. Plant breeding processes for traits or characteristics;
   b. DNA or non-DNA identification;
   c. Identification of seed with desired traits or characteristics for subsequent germination to maturity in a field or green house;
   d. Selection based on presence or absence of desired trait;
   e. Selection based on presence or absence of genetic marker.

Use of information from testing seed is set forth in U.S. Pat. No. 7,227,065, incorporated by reference herein. Examples are as follows.

In addition to phenotypic observations, the genotype of a plant can also be examined. A plant's genotype can be used to identify plants of the same variety or a related variety. For example, the genotype can be used to determine the pedigree of a plant. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

Isozyme Electrophoresis and RFLPs as discussed in Lee, M., "Inbred Lines of Maize and Their Molecular Markers," The Maize Handbook, (Springer-Verlag, New York, Inc. 1994, at 423-432) incorporated herein by reference, have been widely used to determine genetic composition. Isozyme Electrophoresis has a relatively low number of available markers and a low number of allelic variants. RFLPs allow more discrimination because they have a higher degree of allelic variation in maize and a larger number of markers can be found. Both of these methods have been eclipsed by SSRs as discussed in Smith et al., "An evaluation of the utility of SSR loci as molecular markers in maize (Zea mays L.): comparisons with data from RFLPs and pedigree", Theoretical and Applied Genetics (1997) vol. 95 at 163-173 and by Pejic et al., "Comparative analysis of genetic similarity among maize inbreds detected by RFLPs, RAPDs, SSRs, and AFLPs," Theoretical and Applied Genetics (1998) at 1248-1255 incorporated herein by reference. SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

Maize DNA molecular marker linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference.

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Single Nucleotide Polymorphisms (SNPs) and Simple Sequence Repeats (SSRs) may be used in plant breeding methods.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection.

The goal of plant breeding is to combine, in a single variety or hybrid, various desirable traits. For field crops, these traits may include resistance to diseases and insects, resistance to heat and drought, reducing the time to crop maturity, greater yield, and better agronomic quality. With mechanical harvesting of many crops, uniformity of plant characteristics such as germination, stand establishment, growth rate, maturity, and plant and ear height is important. Traditional plant breeding is an important tool in developing new and improved commercial crops.

Field crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line. The term "cross pollination" and "out-cross" as used herein do not include self pollination or sib pollination.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

Maize (Zea mays L.), often referred to as corn in the United States, can be bred by both self-pollination and cross-pollination techniques. Maize has separate male and female flowers on the same plant, located on the tassel and the ear, respectively. Natural pollination occurs in maize when wind blows pollen from the tassels to the silks that protrude from the tops of the ears.

The development of a hybrid maize variety in a maize plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 95% or more of its loci.

During the inbreeding process in maize, the vigor of the lines decreases. Vigor is restored when two different inbred lines are crossed to produce the hybrid progeny (F1). An important consequence of the homozygosity and homogeneity of the inbred lines is that the hybrid between a defined pair of inbreds may be reproduced indefinitely as long as the homogeneity of the inbred parents is maintained. Once the inbreds that create a superior hybrid have been identified, a continual supply of the hybrid seed can be produced using these inbred parents and the hybrid corn plants can then be generated from this hybrid seed supply.

An inbred line may be used to produce a single cross hybrid, a double cross hybrid, or a three-way hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. In each case, pericarp tissue from the female parent will be a part of and protect the hybrid seed.

Large scale commercial maize hybrid production, as it is practiced today, requires the use of some form of male sterility system which controls or inactivates male fertility. A reliable method of controlling male fertility in plants also offers the opportunity for improved plant breeding. This is especially true for development of maize hybrids, which relies upon some sort of male sterility system. There are several ways in which a maize plant can be manipulated so that is male sterile. These include use of manual or mechanical emasculation (or detasseling), cytoplasmic genetic male sterility, nuclear genetic male sterility, gametocides and the like.

Hybrid maize seed is often produced by a male sterility system incorporating manual or mechanical detasseling. Alternate strips of two inbred varieties of maize are planted in a field, and the pollen-bearing tassels are removed from one of the inbreds (female) prior to pollen shed. Providing that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system can be blended to insure that adequate pollen loads are available for fertilization when the hybrid plants are grown. CMS systems have been successfully used since the 1950's, and the male sterility trait is routinely backcrossed into inbred lines. See Wych, p. 585-586, 1998.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. These and all patents referred to are incorporated by reference. In addition to these methods, Albertsen et al., of Pioneer Hi-Bred, U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see Fabinjanski, et al. EPO 89/3010153.8 Publication No. 329, 308 and PCT Application PCT/CA90/00037 published as WO 90/08828).

Another system useful in controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

The use of male sterile inbreds is but one factor in the production of maize hybrids. The development of maize hybrids in a maize plant breeding program requires, in general, the development of homozygous inbred lines, the crossing of these lines, and the evaluation of the crosses. Maize plant breeding programs combine the genetic backgrounds from two or more inbred lines or various other germplasm sources into breeding populations from which new inbred lines are developed by selfing and selection of desired phenotypes. Hybrids also can be used as a source of plant breeding material or as source populations from which to develop or derive new maize lines. Plant breeding techniques known in the art and used in a maize plant breeding program include, but are not limited to, recurrent selection, mass selection, bulk selection, backcrossing, making double haploids, pedigree breeding, open pollination breeding, restriction fragment length polymorphism enhanced selection, genetic marker enhanced selection, and transformation. Often combinations of these techniques are used. The inbred lines derived from hybrids can be developed using plant breeding techniques as described above. New inbreds are crossed with other inbred lines and the hybrids from these crosses are evaluated to determine which of those have commercial potential. The oldest and most traditional method of analysis is the observation of phenotypic traits but genotypic analysis may also be used. Descriptions of breeding methods can also be found in one of several reference books (e.g., Allard, Principles of Plant Breeding, 1960; Simmonds, Principles of Crop Improvement, 1979; Fehr, "Breeding Methods for Cultivar Development", Production and Uses, 2 ed., Wilcox editor, 1987).

Backcrossing can be used to improve inbred lines and a hybrid which is made using those inbreds. Backcrossing can be used to transfer a specific desirable trait from one line, the donor parent, to an inbred called the recurrent parent which has overall good agronomic characteristics yet that lacks the desirable trait. This transfer of the desirable trait into an inbred with overall good agronomic characteristics can be accomplished by first crossing a recurrent parent to a donor parent (non-recurrent parent). The progeny of this cross is then mated back to the recurrent parent followed by selection in the resultant progeny for the desired trait to be transferred from the non-recurrent parent. Typically after four or more backcross generations with selection for the desired trait, the progeny will contain essentially all genes of the recurrent parent except for the genes controlling the desired trait. But the number of backcross generations can be less if molecular markers are used during the selection or elite germplasm is used as the donor parent. The last backcross generation is then selfed to give pure breeding progeny for the gene(s) being transferred.

Backcrossing can also be used in conjunction with pedigree breeding to develop new inbred lines. For example, an F1 can be created that is backcrossed to one of its parent lines to create a BC1. Progeny are selfed and selected so that the newly developed inbred has many of the attributes of the recurrent parent and yet several of the desired attributes of the non-recurrent parent.

Recurrent selection is a method used in a plant breeding program to improve a population of plants. The method entails individual plants cross pollinating with each other to form progeny which are then grown. The superior progeny are then selected by any number of methods, which include individual plant, half sib progeny, full sib progeny, selfed progeny and topcrossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds. Mass selection is a useful technique when used in conjunction with molecular marker enhanced selection as discussed earlier in this application.

The production of double haploids can also be used for the development of inbreds in a breeding program. Double haploids are produced by the doubling of a set of chromosomes (1N) from a heterozygous plant to produce a completely homozygous individual. For example, see Wan et al., "Efficient Production of Doubled Haploid Plants Through Colchicine Treatment of Another-Derived Maize Callus", Theoretical and Applied Genetics, 77:889-892, 1989 and U.S. Patent Application 2003/0005479. This can be advantageous because the process omits the generations of selfing needed to obtain a homozygous plant from a heterozygous source.

Haploid induction systems have been developed for various plants to produce haploid tissues, plants and seed. The haploid induction system can produce haploid plants from any genotype by crossing a selected line (as female) with an inducer line. Such inducer lines for maize include Stock 6 (Coe, 1959, Am. Nat. 93:381-382; Sharkar and Coe, 1966, Genetics 54:453-464), RWS (see Geiger, H. H. 'Application of the in-vivo-haploid induction in hybrid maize breeding'. [online], [retrieved 2008-08-18], KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424); the disclosures of which are incorporated herein by reference.

Methods for obtaining haploid plants are also disclosed in Kobayashi, M. et al., Journ. of Heredity 71(1):9 14, 1980, Pollacsek, M., Agronomie (Paris) 12(3):247-251, 1992; Cho-Un-Haing et al., Journ. of Plant Biol., 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, Maize Genet. Coop. Newsletter 73:53-54; Coe, R. H., 1959, Am. Nat. 93:381-382; Deimling, S. et al., 1997, Vortr. Pflanzenzuchtg 38:203-204; Kato, A., 1999, J. Hered. 90:276 280; Lashermes, P. et al., 1988, Theor. Appl. Genet. 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, Indian J. Genet Plant Breed 38:452-457; Chalyk S. T., 1994, Euphytica 79:13-18; Chase, S. S., 1952, Agron. J. 44:263-267; Coe, E. H., 1959, Am. Nat. 93:381-382; Coe, E. H., and Sarkar, K. R., 1964 J. Hered. 55:231-233; Greenblatt, I. M. and Bock, M., 1967, J. Hered. 58:9-13; Kato, A., 1990, Maize Genet. Coop. Newsletter 65:109-110; Kato, A., 1997, Sex. Plant Reprod. 10:96-100; Nanda, D. K. and Chase, S. S., 1966, Crop Sci. 6:213-215; Sarkar, K. R. and Coe, E. H., 1966, Genetics 54:453-464; Sarkar, K. R. and Coe, E. H., 1971, Crop Sci. 11:543-544; Sarkar, K. R. and Sachan J. K. S., 1972, Indian J. Agric. Sci. 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; U.S. Pat. No. 5,639,951; the disclosures of which are incorporated herein by reference.

Hybrid seed production requires elimination or inactivation of pollen produced by the female parent. Incomplete removal or inactivation of the pollen provides the potential for self-pollination. This inadvertently self-pollinated seed may be unintentionally harvested and packaged with hybrid seed. Also, because the male parent is grown next to the female parent in the field there is the very low probability that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in a hybrid seed bag exists, the occurrence is very low because much care is taken by seed companies to avoid such inclusions. It is worth noting that hybrid seed is sold to growers for the production of grain and forage and not for breeding or seed production. By an individual skilled in plant breeding, these inbred plants unintentionally included in commercial hybrid seed can be identified and selected due to their decreased vigor when compared to the hybrid. Inbreds are identified by their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pages 1-8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) pages 29-42.

Another form of commercial hybrid production involves the use of a mixture of male sterile hybrid seed and male pollinator seed. When planted, the resulting male sterile hybrid plants are pollinated by the pollinator plants. This method is primarily used to produce grain with enhanced quality grain traits, such as high oil, because desired quality grain traits expressed in the pollinator will also be expressed in the grain produced on the male sterile hybrid plant. In this method the desired quality grain trait does not have to be incorporated by lengthy procedures such as recurrent backcross selection into an inbred parent line. One use of this method is described in U.S. Pat. Nos. 5,704,160 and 5,706,603.

There are many important factors to be considered in the art of plant breeding, such as the ability to recognize important morphological and physiological characteristics, the ability to design evaluation techniques for genotypic and phenotypic traits of interest, and the ability to search out and exploit the genes for the desired traits in new or improved combinations.

The objective of commercial maize hybrid line development resulting from a maize plant breeding program is to develop new inbred lines to produce hybrids that combine to produce high grain yields and superior agronomic performance. One of the primary traits breeders seek is yield. However, many other major agronomic traits are of importance in hybrid combination and have an impact on yield or otherwise provide superior performance in hybrid combinations. Such traits include percent grain moisture at harvest, relative maturity, resistance to stalk breakage, resistance to root lodging, grain quality, and disease and insect resistance. In addition, the lines per se must have acceptable performance for parental traits such as seed yields, kernel sizes, pollen production, all of which affect ability to provide parental lines in sufficient quantity and quality for hybridization. These traits have been shown to be under genetic control and many if not all of the traits are affected by multiple genes.

A breeder uses various methods to help determine which plants should be selected from the segregating populations and ultimately which inbred lines will be used to develop hybrids for commercialization. In addition to the knowledge of the germplasm and other skills the breeder uses, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately determined. Statistical analysis includes the calculation of mean values, determination of the statistical significance of the sources of variation, and the calculation of the appropriate variance components. Either a five or one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, pages 261-286 (1987) which is incorporated herein by reference. Mean trait values may be used to determine whether trait differences are significant, and preferably the traits are measured on plants grown under the same environmental conditions.

4. Optional Portable System

Using aspects of the process and apparatus described above, it may be possible to take a portable laser to plants growing in a field or greenhouse, ablate a small portion of a seed or leaf while on the plant, collect or gain access to specific tissue of the plant, and either analyze the tissue there or collect it in a container correlated to an identifier, and take it back to the lab for analysis.

5. Laser Engraving to Cut and Catch Cut Seed on Fly in Blister Pack

Another option is disclosed in FIG. 18. Laser 16 can be adjusted to a cutting mode (e.g., an engraving mode) which can cut, dissect, or separate completely through a seed by appropriate set up. This would allow a whole piece of the seed to be separated and then collected (e.g., well of a blister pack 100A). This could be automated and synchronized so that plural seed can be serially cut up and their cut-off pieces collected. Correlation with the seed from which the pieces came can be maintained. One example is to simultaneously collect each seed in a similarly indexed container (another blister pack 100B).

6. Bulk Segregate Analysis (BSA) of Multiple Seed

It can be possible to use similar methods and apparatus to conduct bulk segregate analysis (BSA) on multiple seed. A tissue removal tool could be set up to remove tissue from multiple seed in the same well, for example a well 40 of a plate 18. The tissue from the multiple seed can then be analyzed by BSA.

FIG. 18 could be used. The cut-off pieces could be collected from multiple seed. Or multiple cut seed could be placed in the same well. Laser ablation could be set to cut up those multiple pieces to sizes that can be used for BSA. Alternatively, a grinding mechanism could grind the seed into mixed fine particles.

One example of BSA is described in S Quarrie et al., "Bulk segregant analysis with molecular markers and its use for improving drought resistance in maize", Journal of Experimental Botany, Vol 50, 1299-1306, Copyright© 1999 by Oxford University Press, which is incorporated by reference herein.

7. Simultaneous Sampling of Multiple Seed

Optionally, plural seed could be sampled simultaneously. One example would be to position plural seed in known locations and then simultaneously remove or expose seed tissue, or a part of each seed. Ways to position plural seed in known locations is shown and described, for example, in U.S. application Ser. No. 12/336,084, filed Dec. 16, 2008, which application is assigned to the owner of the present application and incorporated by reference herein in its entirety. One way to ablate, remove, or expose seed tissue is with a laser (as described herein). One way to ablate, remove, or expose seed tissue simultaneously from a plurality of seed would be to either split a single laser beam into multiple beams, each controlled to the appropriate location of a seed and at a power and with other operating characteristics that ablate or remove seed tissue to create a sample (e.g., a chip from the seed of sufficient size to be useful for analysis). There are a number of ways to split a laser beam for this purpose. A few examples are discussed in U.S. Pat. Nos. 6,562,698 and 6,327,090, which patents are incorporated by reference herein. Others are also possible.

Alternatively, a single head could contain multiple lasers or one or more laser beam splitters, with each laser configured to generate a beam or multiple beams that would ablate or remove tissue from a seed. Still further, there could be multiple heads each with a laser to do so. The system could control the generation and operation of each beam, as well as how it is directed to its corresponding seed. One of skill in the art can calibrate each laser or laser beam, how it is oriented or moved to operating position, and the characteristics of operation to accomplish simultaneous ablation or tissue, chip, or sample removal from multiple seed. For example, a laser configuration that could be used to achieve these embodiments is a galvo head incorporated into a laser.

What is claimed is:

1. A method for selection of seed for production in commercial quantities or for research comprising:
   a. providing one or more candidate seed;
   b. identifying each of the one or more candidate seed;
   c. using a laser beam to remove outer tissue comprising a portion of pericarp from a specified location on a first candidate seed;
   d. performing seed specific analysis of the first candidate seed;
   e. storing data from the seed specific analysis correlated to the unique identification of the first candidate seed; and
   f. using the data in an evaluation of whether the first candidate seed should be selected for production in commercial quantities or for research.

2. The method of claim 1 further comprising comparing the data, or conclusions derived from the data, to similar data or conclusions of other seed.

3. The method of claim 1 further comprising:
   providing a plurality of candidate seed and removing outer tissue from a specified location on a second candidate seed;
   performing seed specific analysis of the second candidate seed;
   storing data from the seed specific analysis correlated to identification of the second candidate seed; and
   using the data in an evaluation of whether the second candidate seed should be selected for production in commercial quantities or for research.

4. The method of claim 3 wherein the evaluation compares the data, or conclusions derived from the data, to similar data or conclusions relating to the first candidate seed.

5. The method of claim 1 wherein the step of removing outer tissue does not materially affect viability or germination of the seed.

6. The method of claim 1 further comprising isolating the seed from other seed.

7. The method of claim 6 wherein isolating the seed comprising placing the seed in a well or cavity having a bottom and sidewall.

8. The method of claim 7 wherein the bottom and sidewall have surface characteristics that diffuse or control reflection of the laser beam.

9. The method of claim 8 wherein the surface characteristics comprise one or more of surface angle relative to the beam, surface texture, surface coating, or surface treatment.

10. The method of claim 1 further comprising automating one or more of steps a through e.

11. The method of claim 1 wherein the seed specific analysis comprises one or more of genetic, chemical, or physical analysis, trait or characteristic analysis, and phenotype analysis.

12. The method of claim 1 wherein the seed comprises an agricultural seed.

13. The method of claim 1 further comprising a plurality of candidate seed, each of the candidate seed having at least one difference from the other comprising one or more of genotype or phenotype.

14. The method of claim 1 wherein the seed comprises corn.

15. The method of claim 1 wherein the portion of pericarp is just enough to expose underlying tissues or structures of interest.

16. The method of claim 15 wherein the underlying tissue or structure comprises an embryo or endosperm.

17. The method of claim 1 further comprising placing the seed in a container in an indexed position correlated to the unique identifier of the seed.

* * * * *